(12) United States Patent
Evans et al.

(10) Patent No.: US 6,809,178 B2
(45) Date of Patent: *Oct. 26, 2004

(54) STEROID-ACTIVATED NUCLEAR RECEPTORS AND USES THEREFOR

(75) Inventors: Ronald M. Evans, La Jolla, CA (US); Bruce Blumberg, Irvine, CA (US)

(73) Assignee: The Salk Institute for Biological Studies, La Jolla, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/227,718

(22) Filed: Jan. 8, 1999

(65) Prior Publication Data

US 2003/0044888 A1 Mar. 6, 2003

Related U.S. Application Data

(63) Continuation-in-part of application No. 09/005,286, filed on Jan. 9, 1998.

(51) Int. Cl.[7] ........................... C07K 14/00; C12Q 1/00; G01N 33/53
(52) U.S. Cl. ........................... 530/350; 435/4; 435/7.8; 436/501; 436/86; 436/87; 930/10
(58) Field of Search ........................... 536/231.1, 24.1; 436/501, 86, 87; 530/350; 930/10; 435/4, 7.8

(56) References Cited

U.S. PATENT DOCUMENTS

| 4,160,152 | A | 7/1979 | Wightman et al. ........... 219/438 |
| 4,256,108 | A | 3/1981 | Theeuwes ................... 128/260 |
| 4,265,874 | A | 5/1981 | Bonsen et al. ................ 424/15 |
| 5,861,274 | A | * | 1/1999 | Evans et al. ................ 435/69.1 |

FOREIGN PATENT DOCUMENTS

| WO | 99/19354 | 4/1999 |
| WO | 99/489915 | 9/1999 |
| WO | 99/61622 | 12/1999 |

OTHER PUBLICATIONS

Crestani et al. Opposing effects of retinoic acid and phorbol esters converge to a common respnse element in the promoter of the rat cholesterol 7alpha–hydroxylase gene (CYP7A). Biochemi. and Biophys. Res. Communications, vol. 225, pp. 585–592 (1996).*

(List continued on next page.)

Primary Examiner—Mary K. Zeman
Assistant Examiner—Lori A. Clow
(74) Attorney, Agent, or Firm—Stephen E. Reiter; Foley & Lardner LLP

(57) ABSTRACT

A novel nuclear receptor, termed the steroid and xenobiotic receptor (SXR), a broad-specificity sensing receptor that is a novel branch of the nuclear receptor superfamily, has been discovered. SXR forms a heterodimer with RXR that can bind to and induce transcription from response elements present in steroid-inducible cytochrome P450 genes in response to hundreds of natural and synthetic compounds with biological activity, including therapeutic steroids as well as dietary steroids and lipids. Instead of hundreds of receptors, one for each inducing compound, the invention SXR receptors monitor aggregate levels of inducers to trigger production of metabolizing enzymes in a coordinated metabolic pathway. Agonists and antagonists of SXR are administered to subjects to achieve a variety of therapeutic goals dependent upon modulating metabolism of one or more endogenous steroids or xenobiotics to establish homeostasis. An assay is provided for identifying steroid drugs that are likely to cause drug interaction if administered to a subject in therapeutic amounts.

17 Claims, 12 Drawing Sheets

OTHER PUBLICATIONS

Sharma et al. Localization of retinoic acid receptors in anterior human embryo. Experimental and Molecular Pathology, vol. 62, pp. 180–189 (1995).*

Palmer et al. Novel sequence determinants in peroxisome proliferator signaling. Journal of Biological Chemistry, vol. 270(27), pp. 16114–16121 (1995).*

Adlercreutz and Mazur, "Phyto–estrogens and Western Diseases," Ann. Med., 29:95–120 (1997).

Altschul et al., "Basic Local Alignment Search Tool," J Mol. Biol., 215:403–410 (1990).

Baes et al., "A New Orphan Member of the Nuclear Hormone Receptor Superfamily That Interacts with a Subset of Retinoic Acid Response Elements," Molecular and Cellular Biology, 14(3):1544–1552 (1994).

Bahouth et al., "Immunological approaches for probing receptor structure and function," TIPS Reviews, 12:338–343 (1991).

Bammel et al., "Divergent effects of different enzyme–inducing agents on endogenous and exogenous testosterone," 42:641–644 (1992).

Barwick et al., "Trans–species Gene Transfer for Analysis of Glucocorticoid–Inducible Transcriptional Activation of Transiently Expressed Human CYP3A4 and Rabbit CYP3A6 in Primary Cultures of Adult Rat and Rabbit Hepatocytes," Molecular Pharmacology, 50:10–16 (1996).

Beato et al., "Steroid Hormone Receptors: Many Actors in Search of a Plot," Cell, 83:851–857 (1995).

Beaune et al., "Isolation and sequence determination of a cDNA clone related to human cytochrome P–450 nifedipine oxidase," Proc. Natl. Acad. Sci., 83:8064–8068 (1986).

Blumberg et al., "Novel retinoic acid receptor ligands in Xenopus embryos," Proc. Natl. Acad. Sci., 93:4873–4878 (1996).

Blumberg et al., "BXR, an embryonic orphan nuclear receptor activated by a novel class of endogenous benzoate metabolites," Genes & Development, 12:1269–1277 (1998).

Burger et al., "Paradoxical transcriptional activation of rat liver cytochrome P–450 3A1 by dexamethasone and the antiglucocorticoid pregnenolone 16α–carbonitrile: Analysis by transient transfection into primary monolayer cultures of adult rat hepatocytes," Proc. Natl. Acad. Sci.(USA), 89:2145–2149 (1992).

Denison and Whitlock, "Xenobiotic–inducible Transcription of Cytochrome P450 Genes," Journal of Biological Chemistry, 270(31):18175–18178 (1995).

Devereux et al., "A comprehensive set of sequence analysis programs for the VAX," Nucleic Acids Research, 12:387–395 (1984).

Edwards et al., "Changes in Cortisol Metabolism Following Rifampicin Therapy," The Lancet, 2:549–551 (1974).

Elshourbagy and Guzelian, "Separation, Purification, and Characterization of a Novel Form of Hepatic Cytochrome P–450 from Rats Treated with Pregnenolone–16α–carbonitrile," Journal of Biological Chemistry, 255:1279–1285 (1980).

Enmark and Gustafsson, "Orphan Nuclear Receptors—The First Eight Years," Mol. Endo., 10(11):1293–1307 (1996).

Evans, Ronald M., "The Steroid and Thyroid Hormone Receptor Superfamily," Science, 240:889–895 (1988).

Fernandez–Salguero and Gonzalez, "The CYP2A gene subfamily: species defferences, regulation, catalytic activities and role in chemical carcinogenesis," Pharmacogenetics, 5:S123–S128 (1995).

Forman et al., "Unique Response Pathways Are Established by Allosteric Interactions among Nuclear Hormone Receptors," Cell, 81:541–550 (1995).

Forman et al., "Hypolipidemic drugs, polyunsaturated fatty acids, and eicosanoids are ligands for peroxisome proliferator–activated receptors α and δ," Proc. Natl. Acad. Sci. USA, 94:4312–4317 (1997).

Gonzalez et al., "Complete cDNA and Protein Sequence of a Pregnenolone 16α–Carbonitrile–induced Cytochrome P–450," Journal of Biological Chemistry, 260(12):7435–7441 (1985).

Gonzalez et al., "Pregnenolone 16α–Carbonitrile–Inducible P–450 Gene Family: Gene Conversion and Differential Regulation," Molecular and Cellular Biology, 6(8):2969–2976 (1986).

Gonzalez, Frank J., "Human cytochromes P450: problems and prospects," TIPS Reviews, 13:346–352 (1992).

Gottlicher et al., "Fatty acids activate a chimera of the clofibric acid–activated receptor and the glucocorticoid receptor," Proc. Natl. Acad. Sci. USA, 89:4653–4657 (1992).

Guengerich, F. Peter, "Metabolism of 17αEthynylestradiol in Humans", Life Sciences, 47:1981–1988 (1990).

Hankinson, Oliver, "The Aryl Hydrocarbon Receptor Complex," Annu. Rev. Pharmacol. Toxicol. 35:307–340 (1995).

Hardwick et al., "Cloning of DNA Complementary to Cytochrome P–450 Induced by Pregnenolone–16αcarbonitrile," Journal of Biological Chemistry, 258:10182–10186 (1983).

Henikoff and Henikoff, "Amino acit substitution matrices from protein blocks," Proc. Natl. Acad. Sci. USA, 89:10915–10919 (1992).

Heuman et al., "Immunochemical Evidence for Induction of a Common Form of Hepatic Cytochrome P–450 in Rats Treated with Pregnenolone–16α–carbonitrile or other Steroidal on Non–Steroidal Agents," Molecular Pharmacology, 21:753–760 (1982).

Hollenberg et al., "Primary structure and experssion of a functional human glucocorticoid receptor cDNA," Nature, 318(6047):635–641 (1985).

Hollenberg et al., "Colocalization of DNA–Binding and Transcriptional Activation Functions in the Human Glucocorticoid Receptor," Cell, 49:39–46 (1987).

Holtbecker et al., "The Nifedipine–Rifampin Interaction: Evidence for Induction of Gut Wall Metabolism," Drug Metabolism and Disposition, 24(10):1121–1123 (1996).

Jonat et al., "Antitumor Promotion and Antiinflammation: Down–Modulation of AP–1 (Fos/Jun) Activity by Glucocorticoid Hormone," Cell, 62:1189–1204 (1990).

Juchau, M.R., "Substrate Specificities and Functions of the P450 Cytochromes," Life Sciences, 47:2385–2394 (1990).

Kliewer et al., "Fatty acids and eicosanoids regulate gene expression through direct interactions with peroxisome proliferator–activated receptors α and γ," Proc. Natl. Acad. Sci. USA, 94:4318–4323 (1997).

Kliewer et al., "An Orphan Nuclear Receptor Activated by Pregnanes Defines a novel Steroid Signaling Pathway," Cell, 92:73–82 (1998).

Kolars et al., "First–pass metabolism of cyclosporin by the gut," Lancet, 338:1488–1490 (1991).

Kolars et al., "Identification of Rifampin–inducible P450111A4 (CYP3A4) in Human Small Bowel Enterocytes," Journal of Clinical Investigation, Inc., 90:1871–1878 (1992).

Kyriazopoulou et al., "Rifampicin–Induced Adrenal Crisis In Addisonian Patients Receiving Corticosteroid Replacement Therapy," *Journal of Clinical Endocrinology and Metabolism*, 59(6):1204–1206 (1984).

Kyriazopoulou and Vagenakis, "Abnormal Overnight Dexamethasone Suppression Test in Subjects Receiving Rifampicin Therapy," *Journal of Clinical Endocrinology and Metabolism*, 75(1):315–317 (1992).

Ladias and Karathanasis, "Regulation of the Apolipoprotein AI Gene by ARP–1 a Novel Member of the Steroid Receptor Superfamily," *Science*, 251:561–565 (1991).

Lee et al., "Time course of the changes in prednisolone pharmacokinetics after co–administration or discontinuation of rifampin," *Eur. Journal of Clinical Pharmacology*, 45:287–289 (1993).

Li and Evans, "Ligation independent cloning irrespective of restriction site compatibility," *Nucleic Acids Research*, 25:4165–4166 (1997).

Lonning et al., "Plasma Levels of Estradiol, Estrone, Estrone Sulfate and Sex Hormone Binding Globulin in Patients Receiving Rifampicin," *J. Steroid Biochem.*, 33(4A):631–635 (1989).

Mangelsdorf et al., "The Nuclear Receptor Superfamily: The Second Decade," *Cell*, 83:835–839 (1995).

Mangelsdorf and Evans, "The RXR Heterodimers and Orphan Receptors," *Cell*, 83:841–850 (1995).

McAllister et al., "Rifampicin reduces effectiveness and bioavailability of prednisolone," *British Medical Journal*, 286:923–925 (1983).

Miyata et al., "Transcriptional Elements Directing a Liver–Specific Expression of P450/6βA (CYP3A2) Gene–Encoding Testosterone 6β–Hydroxylase," *Archives of Biochemistry and Biophysics*, 318(1):71–79 (1995).

Molowa et al., "Complete cDNA sequence of a cytochrome P–450 inducible by glucocorticoids in human liver," *Proc. Natl. Acad, Sci. USA*, 83:5311–5315 (1986).

Nebert, Daniel W., "P450 Genes: Structure, Evolution, and Regulation," *Ann. Rev. Biochem.*, 56:945–993 (1987).

Needleman and Wunsoh, "A General Method Applicable to the Search for Similarities in the Amino Acid Sequence of Two Proteins," *Journal of Molecular Biology*, 48:443–453 (1970).

O'Malley and Conneely, "Orphan Receptors: In Search of a Unifying Hypothesis for Activation," *Molecular Endocrinology*, 6:1359–1361 (1992).

Ogura and Evans, "A retinoic acid–triggered cascade of HOXB1 gene activation," *Proc. Natl. Acad. Sci. USA*, 92:387–391 (1995).

Ohnhaus et al., "Urinary Excretion of 6β–Hydroxycortisol and the Time Course Measurement of Enzyme Induction in Man," *Eur. J. Clin. Pharmacol.*, 36:39–46 (1989).

Quattrochi et al., "A Novel cis–Acting Element in a Liver Cytochrome P450 3A Gene Confers Synergistic Induction by Glucocorticoids plus Antiglucocorticoids," *Journal of Biological Chemistry*, 270 (48):28917–28923 (1995).

Russell and Wilson, "Steroid 5α–Reductase: Two Genes/ Two Enzymes," *Annu. Rev. Biochem.*, 63:25–61 (1994).

Schuetz et al, "Induction of Cytochrome P–450 by Glucocorticoids in Rat Liver," *Journal of Biological Chemisry*, 259(3):1999–2006 (1984).

Schuetz and Guzelian, "Induction of Cytochrome P–450 by Glucocorticoids in Rat Liver," *Journal of Biological Chemistry*, 259(3):2007–2012 (1984).

Schule et al., "Functional Antagonism between Oncoprotein c–Jun and the Glucocorticoid Receptor," *Cell*, 62:1217–1226 (1990).

Selye, H., "Hormones and Resistance," *Journal of Pharmaceutical Sciences*, 60(1):1–28 (1971).

Sucov et al., "Characterization of an autoregulated response element in the mouse retinoic acid receptor type β gene," *Proc. Natl. Acad. Sci. USA*, 87:5392–5396 (1990).

Staden, Rodger, "The current status and portability of our sequence banding software," *Nucleic Acids Research*, 14(1):217–231 (1986).

Terzolo et al., "Misdiagnosis of Cushing's Syndrome in a Patient Receiving Rifampicin Therapy for Tuberculosis," *Horm. Metab. Res.*, 27:148–150 (1995).

Umesono et al., "Direct Repeats as Selective Response Elements for the Thyroid Hormone, Retinoic Acid, and Vitamin $D_3$ Receptors," *Cell*, 65:1255–1266 (1991).

Watkins et al., "Erythromycin Breath Test as an Assay of Gulcocorticoid–inducible Liver Cytochromes P–450," *J. Clin. Invest.*, 83:688–697 (1989).

Wietholtz et al., "Stimulation of bile acid 6α–hydroxylation by rifampin," *Journal of Hepatology*, 24:713–718 (1996).

Willy et al., "LXR, a nuclear receptor that defines a distinct retinoid response pathway," *Genes & Development*, 9:1033–1045 (1995).

Wurtz et al., "A canonical structure for the ligand–binding domain of nuclear receptors," *Nature Structrual Biology*, 3:87–94 1996).

Yang–Yen et al., "Transcriptional Interference between c–Jun and the Glucocorticoid Receptor: Mutual Inhibition of DNA Binding Due to Direct Protein–Protein Interaction," *Cell*, 62:1205–1215 (1990).

Zawawi et al., "The Effects of Therapy with Rifampicin and Isoniazid on Basic Investigations for Cushing's Syndrome," *Ir. j. Med. Sct.*, 165:300–302 (1996).

\* cited by examiner

```
ggcacgagga gatctaggtt caaattaatg ttgccoctag tggtaaagga cagagaccct    60
cagactgatg aaatgcgctc agaattactt agacaaagcg gatatttgcc actctcttcc  120
cctttcctg tgttttgta gtgaagagac ctgaaagaaa aagtaggga gaacataatg     180
agaacaaata cggtaatctc ttcatttgct ag ttcaagtg ctggacttgg gacttaggag 240
gggcaatgga gccgcttagt gcctacatct gacttggact gaaatatagg tgagagacaa  300
gattgtctca tatccgggga aatcataacc tatgactagg acgggaagag gaagcactgc  360
ctttacttca gtgggaatct cggcctcagc ctgcaagcca agtgttcaca gtgagaaaag  420
caagagaata agctaatact cctgtcctga acaaggcagc ggctccttgg taaagctact  480
ccttgatcga tccttgcac cggattgttc aaagtggacc ccaggggaga agtcggagca   540
aagaacttac caccaagcag tccaagaggc cagaagcaa ac ctg gag gtg aga      594
                                                Met Glu Val Arg
                                                 1
```

```
ccc aaa gaa agc tgg aac cat gct gac ttt gta cac tgt gag gac aca    642
Pro Lys Glu Ser Trp Asn His Ala Asp Phe Val His Cys Glu Asp Thr
 5               10                  15                  20
```

```
gag tct gtt cct gga aag ccc agt gtc aac gca gat gag gaa gtc gga   690
Glu Ser Val Pro Gly Lys Pro Ser Val Asn Ala Asp Glu Glu Val Gly
                25                  30                  35
```

```
ggt ccc caa atc tgc cgt gta tgt ggg gac aag gcc act ggc tat cac   738
Gly Pro Gln Ile Cys Arg Val Cys Gly Asp Lys Ala Thr Gly Tyr His
            40                  45                  50
```

```
ttc aat gtc atg aca tgt gaa gga tgc aag ggc ttt ttc agg agg gcc   786
Phe Asn Val Met Thr Cys Glu Gly Cys Lys Gly Phe Phe Arg Arg Ala
        55                  60                  65
```

```
atg aaa cgc aac gcc cgg ctg agg tgc ccc ttc cgg aag ggc gcc tgc   834
Met Lys Arg Asn Ala Arg Leu Arg Cys Pro Phe Arg Lys Gly Ala Cys
    70                  75                  80
```

```
gag atc acc cgg aag acc cgg cga cag tgc cag gcc tgc cgc ctg cgc   882
Glu Ile Thr Arg Lys Thr Arg Arg Gln Cys Gln Ala Cys Arg Leu Arg
 85                  90                  95                 100
```

```
aag tgc ctg gag agc ggc atg aag aag gag atg atc atg tcc gac gag   930
Lys Cys Leu Glu Ser Gly Met Lys Lys Glu Met Ile Met Ser Asp Glu
                105                 110                 115
```

```
gcc gtg gag gag agg cgg gcc ttg atc aag cgg aag aaa agt gaa cgg   978
Ala Val Glu Glu Arg Arg Ala Leu Ile Lys Arg Lys Lys Ser Glu Arg
            120                 125                 130
```

```
aca ggg act cag cca ctg gga gtg cag ggg ctg aca gag gag cag cgg  1026
Thr Gly Thr Gln Pro Leu Gly Val Gln Gly Leu Thr Glu Glu Gln Arg
        135                 140                 145
```

```
atg atg atc agg gag ctg atg gac gct cag atg aaa acc ttt gac act  1074
Met Met Ile Arg Glu Leu Met Asp Ala Gln Met Lys Thr Phe Asp Thr
    150                 155                 160
```

```
acc ttc tcc cat ttc aag aat ttc cgg ctg cca ggg gtg ctt agc agt  1122
Thr Phe Ser His Phe Lys Asn Phe Arg Leu Pro Gly Val Leu Ser Ser
165                 170                 175                 180
```

FIG. 1A-1

```
ggc tgc gag ttg cca gag tct ctg cag gcc cca tcg agg gaa gaa gct      1170
Gly Cys Glu Leu Pro Glu Ser Leu Gln Ala Pro Ser Arg Glu Glu Ala
            185                 190                 195 gcc aag tgg agc cag gtc cgg aaa gat ctg tgc tct ttg aag gtc tct      1218
Ala Lys Trp Ser Gln Val Arg Lys Asp Leu Cys Ser Leu Lys Val Ser
            200                 205                 210 ctg cag ctg cgg ggg gag gat ggc agt gtc tgg aac tac aaa ccc cca      1266
Leu Gln Leu Arg Gly Glu Asp Gly Ser Val Trp Asn Tyr Lys Pro Pro
            215                 220                 225 gcc gac agt ggc ggg aaa gag atc ttc tcc ctg ctg ccc cac atg gct      1314
Ala Asp Ser Gly Gly Lys Glu Ile Phe Ser Leu Leu Pro His Met Ala
            230                 235                 240 gac atg tca acc tac atg ttc aaa ggc atc atc agc ttt gcc aaa gtc      1362
Asp Met Ser Thr Tyr Met Phe Lys Gly Ile Ile Ser Phe Ala Lys Val
245                 250                 255                 260 atc tcc tac ttc agg gac ttg ccc atc gag gac cag atc tcc ctg ctg      1410
Ile Ser Tyr Phe Arg Asp Leu Pro Ile Glu Asp Gln Ile Ser Leu Leu
                265                 270                 275 aag ggg gcc gct ttc gag ctg tgt caa ctg aga ttc aac aca g tg ttc     1458
Lys Gly Ala Ala Phe Glu Leu Cys Gln Leu Arg Phe Asn Thr Val Phe
            280                 285                 290 aac gcg gag act gga acc tgg gag tgt ggc cgg ctg tcc tac tgc ttg      1506
Asn Ala Glu Thr Gly Thr Trp Glu Cys Gl y Arg Leu Ser Tyr Cys Leu
            295                 300                 305 gaa gac act gca ggt ggc ttc cag caa ctt cta ctg gag ccc atg ctg      1554
Glu Asp Thr Ala Gly Gly Phe Gln Gln Leu Leu Leu Glu Pro Met Leu
310                 315                 320 aaa ttc cac tac atg ctg aag aag ctg cag ctg cat gag gag gag tat      1602
Lys Phe His Tyr Met Leu Lys Lys Leu Gln Leu His Glu Glu Glu Tyr
325                 330                 335                 340 gtg ctg atg cag gcc atc tcc ctc ttc tcc cca gac cgc cca ggt gtg      1650
Val Leu Met Gln Ala Ile Ser Leu Phe Ser Pro Asp Arg Pro Gly Val
            345                 350                 355 ctg cag cac cgc gtg gtg gac cag ctg cag gag caa ttc gcc att act      1698
Leu Gln His Arg Val Val Asp Gln Leu Gln Glu Gln Phe Ala Ile Thr
            360                 365                 370 ctg aag tcc tac att gaa tgc aat cgg ccc cag cct gct cat agg ttc      1746
Leu Lys Ser Tyr Ile Glu Cys Asn Arg Pro Gln Pro Ala His Arg Phe
            375                 380                 385 ttg ttc ctg aag atc atg gct atg ctc acc gag ctc cgc agc atc aat      1794
Leu Phe Leu Lys Ile Met Ala Met Leu Thr Glu Leu Arg Ser Ile Asn
390                 395                 400
```

FIG. 1A-2

```
gct cag cac acc cag cgg ctg ctg cgc atc cag gac ata cac ccc ttt    1842
Ala Gln His Thr Gln Arg Leu Leu Arg Ile Gln Asp Ile His Pro Phe
405                 410                 415                 420 gct acg ccc ctc atg cag gag ttg ttc ggt atc aca ggt agc tga        1887
Ala Thr Pro Leu Met Gln Glu Leu Phe Gly Ile Thr Gly Ser
                425                 430 gtggctgtcc ttgggtgaca cctccgagag gtagttagac ccagagccct ctgagtcgcc  1947
actcccgggc caagacagat ggacactgcc aagagccgac aatgccctgc tggcctgtct  2007
ccctagggaa ttcctgctat gacagctggc tagcattcct caggaaggac atggggtgcc  2067
c                                                                  2068
```

FIG. 1A-3

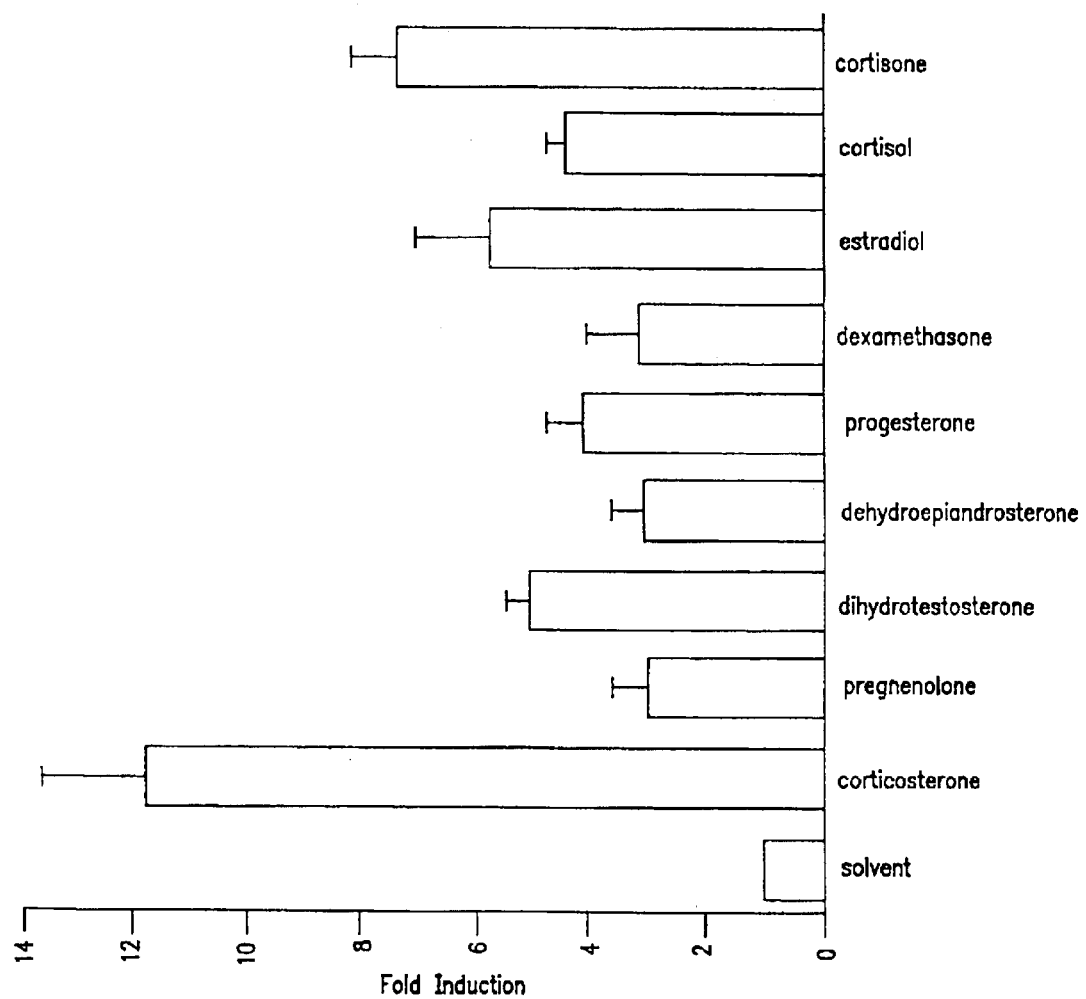

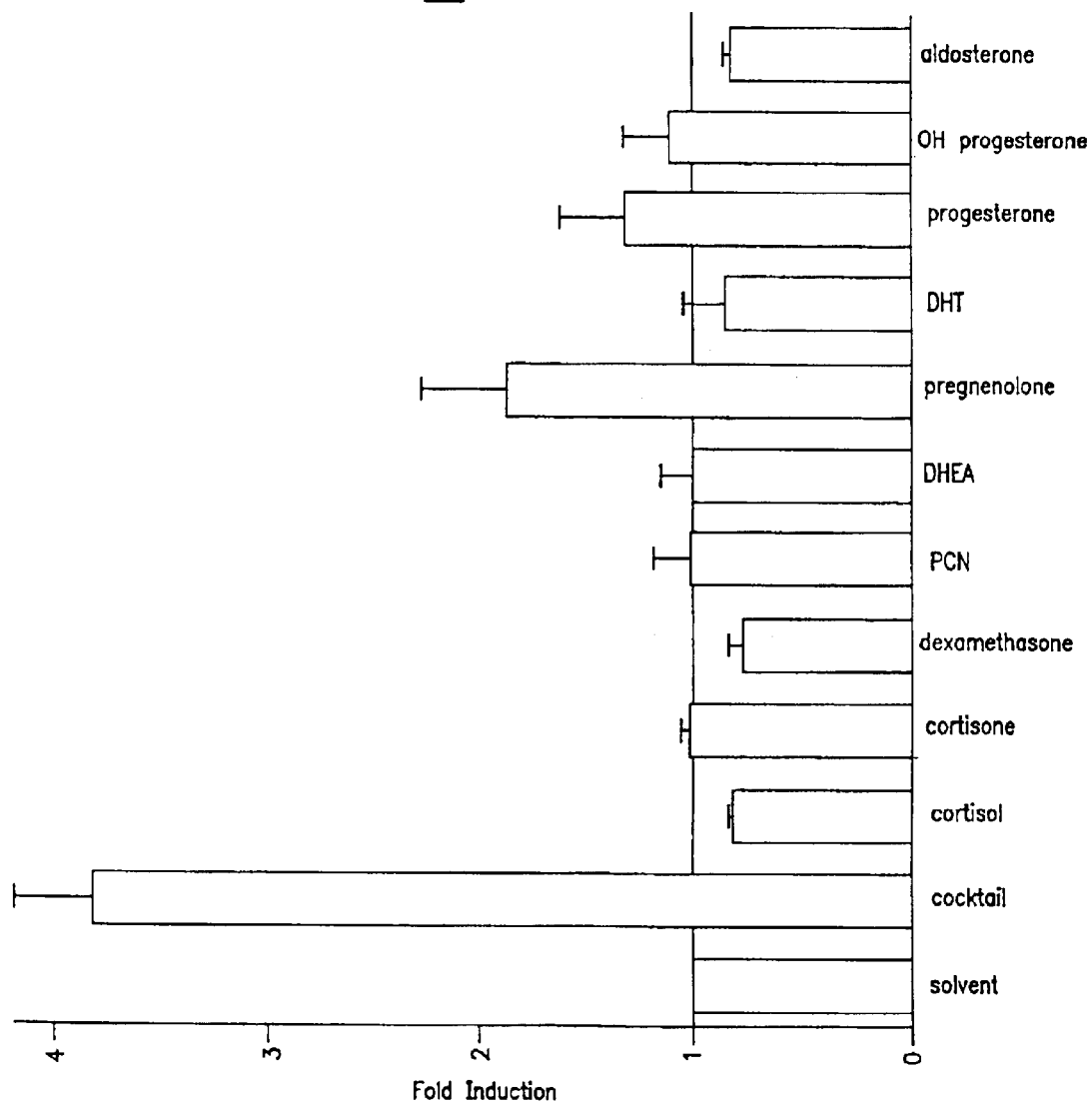

DR-3
rCYP3A1    tagac AGTTCA tga AGTTCA tctac
rCYP3A2    taagc AGTTCA taa AGTTCA tctac
rUGT1A6    actgt AGTTCA taa AGTTCA catgg DR-4
rbCYP2C1   caatc AGTTCA acag GGTTCA ccaat
rP450R       cac AGGTGA gctg AGGCCA gcagc AGGTCG aaa DR-5
rCYP2A1    gtgca GGTTCA actgg AGGTCA acatg
rCYP2A2    gtgct GGTTCA actgg AGGTCA gtatg
rCYP2C6    agtct AGTTCA gtggg GGTTCA gtctt
rCYP2E1    gagat GGTTCA aggaa GGGTCA ttaac

FIG. 6A

CYP3A4    tagaata TGAACT caaagg AGGTCA gtgagtgg
CYP3A5    tagaata TGAACT caaagg AGGTAA gcaaaggg
CYP3A7    tagaata TTAACT caatgg AGGC.A gtgagtgg

FIG. 6B

SEQUENCE LISTING

<160> NUMBER OF SEQ ID NOS: 41

<210> SEQ ID NO 1
<211> LENGTH: 2068
<212> TYPE: DNA
<213> ORGANISM: Homo sapiens
<220> FEATURE:
<221> NAME/KEY: CDS
<222> LOCATION: (583)..(1887)

<400> SEQUENCE: 1

| | | | | | |
|---|---|---|---|---|---|
| ggcacgagga | gatctaggtt | caaattaatg | ttgcccctag | tggtaaagga | cagagaccct     60 |
| cagactgatg | aaatgcgctc | agaattactt | agacaaagcg | gatatttgcc | actctcttcc    120 |
| cctttcctg | tgtttttgta | gtgaagagac | ctgaaagaaa | aaagtaggga | gaacataatg    180 |
| agaacaaata | cggtaatctc | ttcatttgct | agttcaagtg | ctggacttgg | gacttaggag    240 |
| gggcaatgga | gccgcttagt | gcctacatct | gacttggact | gaaatatagg | tgagagacaa    300 |
| gattgtctca | tatccgggga | aatcataacc | tatgactagg | acgggaagag | gaagcactgc    360 |
| ctttacttca | gtgggaatct | cggcctcagc | ctgcaagcca | agtgttcaca | gtgagaaaag    420 |
| caagagaata | agctaatact | cctgtcctga | acaaggcagc | ggctccttgg | taaagctact    480 |
| ccttgatcga | tcctttgcac | cggattgttc | aaagtggacc | ccagggagaa | agtcggagca    540 |

-continued

```
aagaacttac caccaagcag tccaagaggc cagaagcaa ac ctg gag gtg aga         594
                                              Met Glu Val Arg
                                                1 ccc aaa gaa agc tgg aac cat gct gac ttt gta cac tgt gag gac aca       642
Pro Lys Glu Ser Trp Asn His Ala Asp Phe Val His Cys Glu Asp Thr
  5              10                  15                  20 gag tct gtt cct gga aag ccc agt gtc aac gca gat gag gaa gtc gga       690
Glu Ser Val Pro Gly Lys Pro Ser Val Asn Ala Asp Glu Glu Val Gly
                  25                  30                  35 ggt ccc caa atc tgc cgt gta tgt ggg gac aag gcc act ggc tat cac       738
Gly Pro Gln Ile Cys Arg Val Cys Gly Asp Lys Ala Thr Gly Tyr His
              40                  45                  50 ttc aat gtc atg aca tgt gaa gga tgc aag ggc ttt ttc agg agg gcc       786
Phe Asn Val Met Thr Cys Glu Gly Cys Lys Gly Phe Phe Arg Arg Ala
          55                  60                  65 atg aaa cgc aac gcc cgg ctg agg tgc ccc ttc cgg aag ggc gcc tgc       834
Met Lys Arg Asn Ala Arg Leu Arg Cys Pro Phe Arg Lys Gly Ala Cys
      70                  75                  80 gag atc acc cgg aag acc cgg cga cag tgc cag gcc tgc cgc ctg cgc       882
Glu Ile Thr Arg Lys Thr Arg Arg Gln Cys Gln Ala Cys Arg Leu Arg
 85                  90                  95                 100 aag tgc ctg gag agc ggc atg aag aag gag atg atc atg tcc gac gag       930
Lys Cys Leu Glu Ser Gly Met Lys Lys Glu Met Ile Met Ser Asp Glu
                 105                 110                 115 gcc gtg gag gag agg cgg gcc ttg atc aag cgg aag aaa agt gaa cgg       978
Ala Val Glu Glu Arg Arg Ala Leu Ile Lys Arg Lys Lys Ser Glu Arg
                     120                 125                 130 aca ggg act cag cca ctg gga gtg cag ggg ctg aca gag gag cag cgg      1026
Thr Gly Thr Gln Pro Leu Gly Val Gln Gly Leu Thr Glu Glu Gln Arg
                 135                 140                 145 atg atg atc agg gag ctg atg gac gct cag atg aaa acc ttt gac act      1074
Met Met Ile Arg Glu Leu Met Asp Ala Gln Met Lys Thr Phe Asp Thr
                     150                 155                 160 acc ttc tcc cat ttc aag aat ttc cgg ctg cca ggg gtg ctt agc agt      1122
Thr Phe Ser His Phe Lys Asn Phe Arg Leu Pro Gly Val Leu Ser Ser
165                 170                 175                 180 ggc tgc gag ttg cca gag tct ctg cag gcc cca tcg agg gaa gaa gct      1170
Gly Cys Glu Leu Pro Glu Ser Leu Gln Ala Pro Ser Arg Glu Glu Ala
                 185                 190                 195 gcc aag tgg agc cag gtc cgg aaa gat ctg tgc tct ttg aag gtc tct      1218
Ala Lys Trp Ser Gln Val Arg Lys Asp Leu Cys Ser Leu Lys Val Ser
                 200                 205                 210 ctg cag ctg cgg ggg gag gat ggc agt gtc tgg aac tac aaa ccc cca      1266
Leu Gln Leu Arg Gly Glu Asp Gly Ser Val Trp Asn Tyr Lys Pro Pro
                 215                 220                 225 gcc gac agt ggc ggg aaa gag atc ttc tcc ctg ctc ccc cac atg gct      1314
Ala Asp Ser Gly Gly Lys Glu Ile Phe Ser Leu Leu Pro His Met Ala
230                 235                 240 gac atg tca acc tac atg ttc aaa ggc atc atc agc ttt gcc aaa gtc      1362
Asp Met Ser Thr Tyr Met Phe Lys Gly Ile Ile Ser Phe Ala Lys Val
245                 250                 255                 260 atc tcc tac ttc agg gac ttg ccc atc gag gac cag atc tcc ctg ctg      1410
Ile Ser Tyr Phe Arg Asp Leu Pro Ile Glu Asp Gln Ile Ser Leu Leu
                 265                 270                 275 aag ggg gcc gct ttc gag ctg tgt caa ctg aga ttc aac aca gtg ttc      1458
Lys Gly Ala Ala Phe Glu Leu Cys Gln Leu Arg Phe Asn Thr Val Phe
                 280                 285                 290 aac gcg gag act gga acc tgg gag tgt ggc cgg ctg tcc tac tgc ttg      1506
Asn Ala Glu Thr Gly Thr Trp Glu Cys Gly Arg Leu Ser Tyr Cys Leu
```

-continued

```
                    295                 300                 305
gaa gac act gca ggt ggc ttc cag caa ctt cta ctg gag ccc atg ctg    1554
Glu Asp Thr Ala Gly Gly Phe Gln Gln Leu Leu Leu Glu Pro Met Leu
310                 315                 320 aaa ttc cac tac atg ctg aag aag ctg cag ctg cat gag gag gag tat    1602
Lys Phe His Tyr Met Leu Lys Lys Leu Gln Leu His Glu Glu Glu Tyr
325                 330                 335                 340 gtg ctg atg cag gcc atc tcc ctc ttc tcc cca gac cgc cca ggt gtg    1650
Val Leu Met Gln Ala Ile Ser Leu Phe Ser Pro Asp Arg Pro Gly Val
                    345                 350                 355 ctg cag cac cgc gtg gtg gac cag ctg cag gag caa ttc gcc att act    1698
Leu Gln His Arg Val Val Asp Gln Leu Gln Glu Gln Phe Ala Ile Thr
                360                 365                 370 ctg aag tcc tac att gaa tgc aat cgg ccc cag cct gct cat agg ttc    1746
Leu Lys Ser Tyr Ile Glu Cys Asn Arg Pro Gln Pro Ala His Arg Phe
            375                 380                 385 ttg ttc ctg aag atc atg gct atg ctc acc gag ctc cgc agc atc aat    1794
Leu Phe Leu Lys Ile Met Ala Met Leu Thr Glu Leu Arg Ser Ile Asn
        390                 395                 400 gct cag cac acc cag cgg ctg ctg cgc atc cag gac ata cac ccc ttt    1842
Ala Gln His Thr Gln Arg Leu Leu Arg Ile Gln Asp Ile His Pro Phe
405                 410                 415                 420 gct acg ccc ctc atg cag gag ttg ttc ggt atc aca ggt agc tga        1887
Ala Thr Pro Leu Met Gln Glu Leu Phe Gly Ile Thr Gly Ser
                    425                 430 gtggctgtcc ttgggtgaca cctccgagag gtagttagac ccagagccct ctgagtcgcc  1947
actcccgggc caagacagat ggacactgcc aagagccgac aatgccctgc tggcctgtct  2007
ccctagggaa ttcctgctat gacagctggc tagcattcct caggaaggac atggggtgcc  2067
c                                                                   2068

<210> SEQ ID NO 2
<211> LENGTH: 434
<212> TYPE: PRT
<213> ORGANISM: Homo sapiens

<400> SEQUENCE: 2

Met Glu Val Arg Pro Lys Glu Ser Trp Asn His Ala Asp Phe Val His
1               5                   10                  15

Cys Glu Asp Thr Glu Ser Val Pro Gly Lys Pro Ser Val Asn Ala Asp
            20                  25                  30

Glu Glu Val Gly Gly Pro Gln Ile Cys Arg Val Cys Gly Asp Lys Ala
        35                  40                  45

Thr Gly Tyr His Phe Asn Val Met Thr Cys Glu Gly Cys Lys Gly Phe
    50                  55                  60

Phe Arg Arg Ala Met Lys Arg Asn Ala Arg Leu Arg Cys Pro Phe Arg
65                  70                  75                  80

Lys Gly Ala Cys Glu Ile Thr Arg Lys Thr Arg Arg Gln Cys Gln Ala
                85                  90                  95

Cys Arg Leu Arg Lys Cys Leu Glu Ser Gly Met Lys Lys Glu Met Ile
            100                 105                 110

Met Ser Asp Glu Ala Val Glu Glu Arg Arg Ala Leu Ile Lys Arg Lys
        115                 120                 125

Lys Ser Glu Arg Thr Gly Thr Gln Pro Leu Gly Val Gln Gly Leu Thr
    130                 135                 140

Glu Glu Gln Arg Met Met Ile Arg Glu Leu Met Asp Ala Gln Met Lys
145                 150                 155                 160
```

```
Thr Phe Asp Thr Thr Phe Ser His Phe Lys Asn Phe Arg Leu Pro Gly
            165                 170                 175

Val Leu Ser Ser Gly Cys Glu Leu Pro Glu Ser Leu Gln Ala Pro Ser
            180                 185                 190

Arg Glu Glu Ala Ala Lys Trp Ser Gln Val Arg Lys Asp Leu Cys Ser
            195                 200                 205

Leu Lys Val Ser Leu Gln Leu Arg Gly Glu Asp Gly Ser Val Trp Asn
            210                 215                 220

Tyr Lys Pro Pro Ala Asp Ser Gly Gly Lys Glu Ile Phe Ser Leu Leu
225                 230                 235                 240

Pro His Met Ala Asp Met Ser Thr Tyr Met Phe Lys Gly Ile Ile Ser
            245                 250                 255

Phe Ala Lys Val Ile Ser Tyr Phe Arg Asp Leu Pro Ile Glu Asp Gln
            260                 265                 270

Ile Ser Leu Leu Lys Gly Ala Ala Phe Glu Leu Cys Gln Leu Arg Phe
            275                 280                 285

Asn Thr Val Phe Asn Ala Glu Thr Gly Thr Trp Glu Cys Gly Arg Leu
            290                 295                 300

Ser Tyr Cys Leu Glu Asp Thr Ala Gly Gly Phe Gln Gln Leu Leu Leu
305                 310                 315                 320

Glu Pro Met Leu Lys Phe His Tyr Met Leu Lys Lys Leu Gln Leu His
            325                 330                 335

Glu Glu Glu Tyr Val Leu Met Gln Ala Ile Ser Leu Phe Ser Pro Asp
            340                 345                 350

Arg Pro Gly Val Leu Gln His Arg Val Val Asp Gln Leu Gln Glu Gln
            355                 360                 365

Phe Ala Ile Thr Leu Lys Ser Tyr Ile Glu Cys Asn Arg Pro Gln Pro
            370                 375                 380

Ala His Arg Phe Leu Phe Leu Lys Ile Met Ala Met Leu Thr Glu Leu
385                 390                 395                 400

Arg Ser Ile Asn Ala Gln His Thr Gln Arg Leu Leu Arg Ile Gln Asp
            405                 410                 415

Ile His Pro Phe Ala Thr Pro Leu Met Gln Glu Leu Phe Gly Ile Thr
            420                 425                 430

Gly Ser

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Putative SXR response element from the steroid
      hydoxylase, rCYP3A1

<400> SEQUENCE: 3
tagacagttc atgaagttca tctac                                    25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Putative SXR response element from the steroid
      hydoxylase, rCYP3A2

<400> SEQUENCE: 4
taagcagttc ataaagttca tctac                                          25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Putative SXR response element from the steroid
      hydoxylase, rUGT1A6

<400> SEQUENCE: 5
actgtagttc ataaagttca catgg                                          25

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Putative SXR response element from the steroid
      hydoxylase, rbCYP2C1

<400> SEQUENCE: 6
caatcagttc aacagggttc accaat                                         26

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Putative SXR response element from the steroid
      hydoxylase, rP450R

<400> SEQUENCE: 7
cacaggtgag ctgaggccag cagcaggtcg aaa                                 33

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Putative SXR response element from the steroid
      hydoxylase, rCYP2A1

<400> SEQUENCE: 8
gtgcaggttc aactggaggt caacatg                                        27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Putative SXR response element from the steroid
      hydoxylase, rCYP2A2

<400> SEQUENCE: 9
gtgctggttc aactggaggt cagtatg                                           27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Putative SXR response element from the steroid
      hydoxylase, rCYP2C6

<400> SEQUENCE: 10
agtctagttc agtggggtt cagtctt                                            27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Putative SXR response element from the steroid
      hydoxylase, hCYP2E1

<400> SEQUENCE: 11
gagatggttc aaggaagggt cattaac                                           27

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Direct repeat with spacer of 0 nucleotides

<400> SEQUENCE: 12
catagtcagg tcaaggtcag atcaac                                            26

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Direct repeat with spacer of 1 nucleotide

<400> SEQUENCE: 13
catagtcagg tcataggtca gatcaac                                           27

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

-continued

<223> OTHER INFORMATION: Direct repeat with spacer of 2 nucleotides

<400> SEQUENCE: 14
catagtcagg tcaataggtc agatcaac                                     28

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Direct repeat with spacer of 3 nucleotides

<400> SEQUENCE: 15
catagtcagg tcatataggt cagatcaac                                    29

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Direct repeat with spacer of 4 nucleotides

<400> SEQUENCE: 16
catagtcagg tcatataagg tcagatcaac                                   30

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Direct repeat with spacer of 5 nucleotides

<400> SEQUENCE: 17
catagtcagg tcatatatag gtcagatcaa c                                 31

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Direct repeat with spacer of 6 nucleotides

<400> SEQUENCE: 18
catagtcagg tcatatataa ggtcaagatc aac                               33

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Direct repeat with spacer of 7 nucleotides

<400> SEQUENCE: 19
catagtcagg tcatatatat aggtcagatc aac          33

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Direct repeat with spacer of 10 nucleotides

<400> SEQUENCE: 20
catagtcagg tcatatatat ataaggtcag atcaac          36

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Direct repeat with spacer of 15 nucleotides

<400> SEQUENCE: 21
catagtcagg tcatagtagt agtagtagag gtcagatcaa c          41

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(9)
<223> OTHER INFORMATION: n is a nucleotide spacer of 3 nucleotides,
      wherein each n is independently selected from a, t, c or g
<220> FEATURE:
<223> OTHER INFORMATION: Example of a response element suitable for
      practice of the invention method

<400> SEQUENCE: 22
agttcannnt gaact          15

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: n is a nucleotide spacer of 6 nucleotides,
      wherein each n is independently selected from a, t, c or g
<220> FEATURE:
<223> OTHER INFORMATION: Example of a response element suitable for
      practice of the invention method

<400> SEQUENCE: 23
tgaactnnnn nnaggtca          18

<210> SEQ ID NO 24
<211> LENGTH: 18
<212> TYPE: DNA
<213> ORGANISM: Artificial Sequence -continued

```
<220> FEATURE:
<223> OTHER INFORMATION: Description of Artificial Sequence: Synthetic
      oligonucleotide
<220> FEATURE:
<223> OTHER INFORMATION: Inverted repeat with 6 nucleotide spacer found
      in CYP3A4

<400> SEQUENCE: 24
tgaactcaaa ggaggtca                                                   18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Inverted repeat response element with a spacer
      of 0 nucleotides

<400> SEQUENCE: 25
agcttaggtc atgaccta                                                   18

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Inverted repeat response element with spacer of
      1 nucleotide

<400> SEQUENCE: 26
agcttaggtc agtgaccta                                                  19

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Inverted repeat response element with spacer of
      2 nucleotides

<400> SEQUENCE: 27
agcttaggtc acgtgaccta                                                 20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Inverted repeat response element with spacer of
      3 nucleotides

<400> SEQUENCE: 28
agcttaggtc acagtgacct a                                               21

<210> SEQ ID NO 29
<211> LENGTH: 22
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Inverted repeat response element with spacer of
      4 nucleotides

<400> SEQUENCE: 29
agcttaggtc acatgtgacc ta                                       22

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Inverted repeat response element with spacer of
      5 nucleotides

<400> SEQUENCE: 30
agcttaggtc acactgtgac cta                                      23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Inverted repeat response element with spacer of
      6 nucleotides

<400> SEQUENCE: 31
agctttgaac tcaaaggagg tca                                      23

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: IR-M

<400> SEQUENCE: 32
agcttacgtc atgacgta                                            18

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CYP3A oligonucleotide, CYP3A4, tested for
      binding

<400> SEQUENCE: 33
tagaatatga actcaaagga ggtcagtgag tgg                           33

<210> SEQ ID NO 34
<211> LENGTH: 33
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CYP3A oligonucleotide, CYP3A5, tested for
      binding

<400> SEQUENCE: 34
tagaatatga actcaaagga ggtaagcaaa ggg                                    33

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CYP3A oligonucleotide, CYP3A7, tested for
      binding

<400> SEQUENCE: 35
tagaatatta actcaatgga ggcagtgagt gg                                     32

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(9)
<223> OTHER INFORMATION: n is a nucleotide spacer of 3 nucleotides,
      wherein each n is independently selected from a, t, c or g

<400> SEQUENCE: 36
aggtcannna ggtca                                                        15

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(10)
<223> OTHER INFORMATION: n is a nucleotide spacer of 4 nucleotides,
      wherein each n is independently selected from a, t, c or g

<400> SEQUENCE: 37
aggtcannnn aggtca                                                       16

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: n is a nucleotide spacer of 5 nucleotides,
      wherein each n is independently selected from a, t, c or g

<400> SEQUENCE: 38
```

-continued

```
aggtcannnn naggtca                                                17
```

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(10)
<223> OTHER INFORMATION: n is a nucleotide spacer of 4 nucleotides,
      wherein each n is independently selected from a, t, c or g

<400> SEQUENCE: 39

```
agttcannnn tgaact                                                 16
```

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: n is a nucleotide spacer of 5 nucleotides,
      wherein each n is independently selected from a, t, c or g

<400> SEQUENCE: 40

```
agttcannnn ntgaact                                                17
```

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Gly Lys Thr Cys Ala
 1               5

STEROID-ACTIVATED NUCLEAR RECEPTORS AND USES THEREFOR

RELATED APPLICATIONS

This application is a Continuation-in-Part Application of U.S. Ser. No. 09/005,286, filed Jan. 9, 1998.

This invention was made with Government support under Grant No. GM-26444, awarded by the National Institute of Health. The Government has certain rights in the invention.

FIELD OF THE INVENTION

The present invention relates to intracellular receptors, nucleic acids encoding same, and uses therefor. In a particular aspect, the present invention relates to methods for the modulation of physiological response to elevated levels of steroid and/or xenobiotic compounds.

BACKGROUND OF THE INVENTION

Nuclear receptors constitute a large superfamily of ligand-dependent and sequence-specific transcription factors. Members of this family influence transcription either directly, through specific binding to the promoters of target genes (see Evans, in *Science* 240:889–895 (1988)), or indirectly, via protein—protein interactions with other transcription factors (see, for example, Jonat et al., in *Cell* 62:1189–1204 (1990), Schuele et al., in *Cell* 62:1217–1226 (1990), and Yang-Yen et al., in *Cell* 62:1205–1215 (1990)). The nuclear receptor superfamily (also known in the art as the "steroid/thyroid hormone receptor superfamily") includes receptors for a variety of hydrophobic ligands, including cortisol, aldosterone, estrogen, progesterone, testosterone, vitamin $D_3$, thyroid hormone and retinoic acid, as well as a number of receptor-like molecules, termed "orphan receptors" for which the ligands remain unknown (see Evans, 1988, supra). These receptors all share a common structure indicative of divergence from an ancestral archetype.

Lipophilic hormones such as steroids, retinoic acid, thyroid hormone, and vitamin D3 control broad aspects of animal growth, development, and adult organ physiology. The effects of these hormones are mediated by a large superfamily of intracellular receptors that function as ligand-dependent and sequence-specific transcription factors. The non-steroidal nuclear receptors for thyroid hormone (TR), vitamin D3 (VDR), all-trans retinoic acid (RAR), and fatty acids and eicosanoids (PPAR) form heterodimers with the 9-cis retinoic acid receptor (RXR) that bind bipartite hormone-response elements (HREs) composed of directly repeated half sites related to the sequence AGGTCA (Mangelsdorf and Evans, *Cell* 83: 841–850, 1995). In contrast, the steroid receptors function as homodimers and bind to palindromic target sequences spaced by three nucleotides (Beato et al., *Cell* 83: 851–857, 1995). In addition to the known receptors, a large group of structurally-related "orphan" nuclear receptors has been described which possess obvious DNA and ligand binding domains, but lack identified ligands (Mangelsdorf et al., *Cell* 83:835–839, 1995; Enmark and Gustafsson, *Mol. Endocrinol.* 10:1293 (1996); and O'Malley and Conneely, *Mol. Endocrinol.* 6:1359 (1992)). Each has the potential to regulate a distinct endocrine signaling pathway.

It is widely viewed that the hormone response is a consequence of the release, from an endocrine gland, of a ligand that circulates through the blood, and coordinately regulates responses in target tissues by acting through specific nuclear receptors. Hormone responsiveness is dependent on the ability to rapidly clear ligand from the blood and the body so that, in absence of a stimulus, target tissues return to a ground state. Hormonal homeostasis is thus achieved by the coordinated release and degradation of bioactive hormones. Steroid hormones and their many metabolites are primarily inactivated by reduction and oxidation in the liver. Since hundreds of adrenal steroids have been identified (e.g., dozens of each of the sex steroids (androgens, estrogens and progestins), 25–35 vitamin D metabolites, and likely hundreds of fatty acids, eicosanoids, hydroxyfats and related bioactive lipids), the problem of efficient ligand elimination is critical to physiologic homeostasis. In addition to the existence of a myriad of endogenous hormones, a similar diversity of ingested plant and animal steroids and bioactive xenobiotic compounds must also be degraded.

Selye first introduced the concept that exogenous steroids and pharmacologic substances may function to modulate the expression of enzymes that would protect against subsequent exposure to toxic xenobiotic substances (H. Selye, *J. Pharm. Sci.* 60:1–28, 1971). These compounds, which Selye called "catatoxic steroids," are typified by the synthetic glucocorticoid antagonist, pregnenolone-16-carbonitrile (PCN). PCN, and a variety of xenobiotic steroids, induce the proliferation of hepatic endoplasmic reticulum and the expression of cytochrome P450 genes (Burger et al., *Proc. Natl. Acad. Sci. (USA)* 89:2145–2149, 1992; Gonzalez et al., *Mol. Cell. Biol.* 6:2969–2976, 1986; and Schuetz and Guzelian, *J. Biol. Chem.* 259:2007–2012, 1984). One consequence of PCN treatment is the induction of nonspecific "protection" against subsequent exposure to such diverse xenobiotics as digitoxin, indomethacin, barbiturates, and steroids (Selye, supra, 1971).

Furthermore, it is known that a variety of such compounds can activate P450 genes responsible for their detoxification or degradation (Fernandez-Salguero and Gonzalez, *Pharmacogenetics* 5:S123–128, 1995; Denison and Whitlock, *J. Biol. Chem.* 270:18175–18178, 1995; O. Hankinson, *Ann. Rev. Pharmacol. Toxicol.* 35:307–340, 1995; and Rendic and Di Carlo, *Drug Metab. Rev.* 29:413–580, 1997).

While it appears that such catatoxic compounds regulate the expression of cytochrome P450s and other detoxifying enzymes, two lines of evidence argue that such regulation is independent of the classical steroid receptors. First, many of the most potent compounds (e.g., PCN, spironolactone, and cyproterone acetate) have been shown to be steroid receptor antagonists; whereas others (e.g., dexamethasone) are steroid receptor agonists (Burger, supra, 1992). Second, the nonspecific protective response remains after bilateral adrenalectomy (and presumably in the absence of adrenal steroids), but not after partial hepatectomy (Selye, supra, 1971).

Insight into the mechanism by which PCN exerts its catatoxic effects is provided by the demonstration that PCN induces the expression of CYP3A1 and CYP3A2, two closely related members of the P450 family of monooxygenases (see, for example, Elshourbagy and Guzelian in *J. Biol. Chem.* 255:1279 (1980); Heuman et al., in *Mol. Pharmacol.* 21:753 (1982); Hardwick et al., in *J. Biol. Chem.* 258:10182 (1983); Scheutz and Guzelian in *J. Biol. Chem.* 259:2007 (1984); Scheutz et al., in *J. Biol. Chem.* 259:1999 (1984); and Gonzalez et al., in *J. Biol. Chem.* 260:7435 (1985)). The CYP3A hemoproteins display broad substrate specificity, hydroxylating a variety of xenobiotics (e.g., cyclosporin, warfarin and erythromycin), as well as endogenous steroids (e.g., cortisol, progesterone, testosterone and DHEA-sulfate. See, for example, Nebert and Gonzalez in *Ann. Rev. Biochem.* 56:945 (1987) and Juchau in *Life Sci.* 47:2385 (1990)). A PCN response element (which is highly conserved in the CYP3A2 gene promoter) has since been identified in subsequent studies with the cloned CYP3A1 gene promoter (see Miyata et al., in *Archives Biochem. Biophysics* 318:71 (1995) and Quattrochi et al., in *J. Biol. Chem.* 270:28917 (1995)). This response element comprises a direct repeat of two copies of the nuclear receptor half-site consensus sequence AGTTCA.

In addition to inducing CYP3A gene expression, PCN has also been shown to have marked effects on hepatic cholesterol homeostasis. These effects include significant decreases in the levels of HMG-CoA reductase and cholesterol 7a-hydroxylase gene expression, with associated reductions in sterol biosynthesis and bile acid secretion. PCN has also been reported to enhance the formation of cholesterol esters and the hypersecretion of cholesterol into the bile. Thus, PCN affects key aspects of cholesterol metabolism, including its biosynthesis, storage and secretion.

Activation of orphan nuclear receptor(s) by catatoxic steroids provides a possible mechanism for the induction of xenobiotic metabolizing enzymes by compounds that do not activate known steroid receptors. Because such enzymes are activated by high (pharmacological) doses of xenobiotic and natural steroids, such a "sensor" would be expected to be a broad-specificity, low-affinity receptor. Such receptors could be activated not only by endogenous steroids and metabolites but also by exogenous compounds such as phytosteroids, xenobiotics and pharmacologic inducers. Indeed, it is known that a variety of such compounds can activate P450 genes responsible for their detoxification or degradation (see, for example, Fernandez-Salguero and Gonzalez in *Pharmacogenetics* 5:S123 (1995); Denison and Whitlock, Jr. in *J. Biol. Chem.* 270:18175 (1995); Hankinson in *Ann. Rev. Pharmacol. Toxicol.* 35:307 (1995); and Rendic and Di Carlo in *Drug Metab. Rev.* 29:413 (1997)).

In healthy individuals, steroid levels are tightly regulated, with increased catabolism of endogenous steroids being compensated by the pituitary releasing an increase of ACTH, which stimulates biosynthesis, and maintenance of plasma steroid levels. The increased catabolism is reflected by elevated urinary levels of steroid metabolites. Indeed, it is already known that treatment with rifampicin increases urinary metabolites, such as 6β-hydroxycortisol (Ohnhaus et al., *Eur. J. Clin. Pharmacol.* 36:39–46, 1989; and Watkins et al., *J. Clin. Invest.,* 83:688–697, 1989), and bile acid metabolites, such as 6β-hydroxy hyocholic and 6α-hyodeoxycholic acids (Wietholtz et al., *J. Hepatol,* 24:713–718, 1996), while the plasma levels of many circulating steroids rise slightly due to increased synthesis (Lonning et al., *J. Steroid Biochem.* 33:631–635, 1989; Bammel et al., *Eur. J. Clin. Pharmacol,* 42:641–644, 1992; and Edwards et al., *Lancet* 2:548–551, 1974).

When synthetic steroids, such as prednisolone (McAllister et al., *Br. Med. J.* 286:923–925, 1983; and Lee et al., *Eur. J. Clin. Pharmaco.* 45:287–289, 1993) or 17α-ethynylestradiol (F. P. Guengerich, *Life Sci.,* 47:1981–1988, 1990) are administered together with rifampicin, plasma levels are rapidly decreased due to enhanced urinary clearance. In some patients undergoing rifampicin therapy for tuberculosis, the increase in urinary steroid levels has led to misdiagnosis of Cushing's syndrome (Kyriazopoulou and Vagenakis, *J. Clin. Endocrinol. Metab.,* 75:315–317, 1992; Zawawi et al., *Ir. J. Med. Sci.,* 165:300–302, 1996; and Terzolo et al., *Horm. Metab. Res.,* 27:148–150, 1995). In these patients, steroid production and clearance normalized when rifampicin was withdrawn. In patients with Addison's disease, who mostly lack the ability to synthesize adrenal steroids, rifampicin treatment leads to rapid depletion of endogenous and administered steroids. These documented clinical situations confirm that induction of CYP3A4 causes increased steroid catabolism (Kyriazopoulou et al., *J. Clin. Endocrinol Metab.* 59:1204–1206, 1984; and Edwards, supra, 1974). However, the art is silent regarding the mechanism by which steroid metabolism is regulated in the body.

Although therapeutically administered steroids are beneficial in achieving therapeutic goals, such compounds can, in some cases, increase the overall level of steroids and xenobiotics above physiologically compatible levels in the subjects to whom they are administered. In other cases, the increased level of steroids and/or xenobiotics may linger in the body longer than is therapeutically required. In addition, some subjects are treated with combinations of steroids and xenobiotics that may be administered separately to treat different conditions, but which, in combination, have an additive, or even synergistic, effect known as a drug interaction. In such cases, the patient may be unaware when a physiologically incompatible level of steroids and xenobiotics has been reached, or when an otherwise therapeutic amount of a steroid becomes potentially dangerous due to combined effects of separately administered drugs.

Accordingly, there is still a need in the art for the identification and characterization of broad specificity, low affinity receptors that participate in the mediation of the physiological effect(s) of steroids and xenobiotics, particularly when combinations of such compounds disrupt homeostasis or cause drug interaction.

SUMMARY OF THE INVENTION

In accordance with the present invention, we have isolated and characterized an example of a novel class of human orphan nuclear receptor, termed the steroid and xenobiotic receptor (SXR). SXR is expressed almost exclusively in the liver, the primary site of xenobiotic and steroid catabolism. Unlike classical steroid receptors, SXR heterodimerizes with RXR and binds to directly repeated sequences related to the half-site, AGTTCA. SXR can activate transcription through response elements found in some steroid inducible P450 genes in response to an enormous variety of natural and synthetic steroid hormones, including antagonists such as PCN, as well as xenobiotic drugs, and bioactive dietary compounds, such as phytoestrogens. The ability of SXR to regulate expression of catabolic enzymes in response to this diversity of steroid and/or xenobiotic compounds provides a novel mechanism for direct regulation of metabolism so as to achieve physiologic homeostasis with respect to such steroid and/or xenobiotic compounds—ideal properties for a "steroid sensing receptor" which mediates the physiological effect(s) of hormones. SXR represents the first new class of steroid receptors described since the identification of the mineralocorticoid receptor ten years ago.

In accordance with a particular aspect of the present invention, there are also provided nucleic acid sequences encoding the above-identified receptors, as well as constructs and cells containing same, and probes derived therefrom. Furthermore, it has also been discovered that a wide variety of substrates modulate the transcription activating effects of invention receptors.

An important requirement for physiologic homeostasis is the removal and detoxification of various endogenous hormones and xenobiotic compounds with biological activity. Much of the detoxification is performed by cytochrome P450 enzymes, many of which have broad substrate specificity and are inducible by a bewildering array of compounds, including steroids. The ingestion of dietary steroids and lipids induces the same enzymes and, thus, must be integrated into a coordinated metabolic pathway. Instead of possessing hundreds of receptors, one for each inducing compound, a class of broad-specificity, low-affinity nuclear receptors has been discovered that monitor total steroid levels and induce the expression of genes encoding xenobiotic metabolizing enzymes. SXR, which is a member of a novel branch of the nuclear receptor superfamily, forms part of a steroid sensor mechanism for removal of elevated levels of steroids and/or xenobiotic compounds from circulation via broad-specificity, low-affinity receptors that represent a novel branch of the nuclear receptor superfamily.

BRIEF DESCRIPTION OF THE FIGURES

FIG. 1 illustrates that SXR is a novel orphan nuclear receptor.

FIGS. 1A-1, 1A-2 and 1A-3 collectively show the sequence of the longest SXR cDNA clone (SEQ ID NO: 1) and a corresponding encoded protein (amino acids 1–434 of SEQ ID NO: 2).

FIG. 2 illustrates that SXR is activated by many steroids. Chimeric receptors composed of the GAL4 DNA-binding domain and the SXR-ligand binding domain were cotransfected into CV-1 cells with the reporter gene tk(MH100)$_4$-luc (Forman et al., *Cell* 81:541–550, 1995). Results are shown as fold induction over solvent (DMSO) control for 50 μM of steroid and represent the averages and standard error from triplicate assays. Neither reporter alone, nor reporter plus GAL4-DBD, was activated by any of these compounds. Column 1.=solvent; column 2=corticosterone; column 3=pregnenolone; column 4=dihydrotestosterone (DHT); column 5=dehydroepiandrosterone; column 6=progesterone; column 7=dexamethasone; column 7=estradiol; column 8=cortisol; and column 9=cortisone.

FIG. 3 illustrates the ability of steroidal activators to act additively. Thus, the ability of steroidal activators to act additively was tested using full-length SXR and the reporter tk(LXRE)$_3$-luc (see Willy et al., in *Genes Dev.* 9:1033 (1995)). The cocktail contained 10 mM of each steroid for an overall concentration of 100 mM total steroid. The cocktail and its individual components were tested at 100, 10 and 1 mM; results are shown in the Figure for 100 mM cocktail and 10 mM aliquots of the component steroids.

FIGS. 6A–C are a series of illustrations indicating that SXR can activate responsive elements found in various steroid and xenobiotic inducible P450 enzymes.

FIG. 6A presents a schematic comparison of nucleotide sequences (SEQ ID NOS 3–11, respectively in order of appearance) encoding response elements found in inducible cytochrome P450 enzymes. A database search for repeats of the sequence RGKTCA (SEQ ID NO: 41) was performed and some of the matches for enzymes involved in hepatic steroid hydroxylation are indicated. The standard nomenclature for P450 enzymes has been utilized. P450R is the single P450 oxidoreductase required for hydroxylation of steroids. UGT1A6 is a rat uridine diphosphate (UDP)-glucuronosyltransferase that conjugates glucuronic acid to hydroxylated steroids.

FIG. 6B presents a schematic comparison of conserved glucocorticoid-response elements found in human CYP3 genes. The region of human CYP3A4 (SEQ ID NO: 33) shown in necessary and sufficient for glucocorticoid and rifampicin induction of the full-length promoter. Corresponding regions of CYP3A5 (SEQ ID NO: 34) and CYP3A7 (SEQ ID NO: 35) are shown (Barwick et al., *Mol. Pharmacol.* 50:10–16, 1996).

FIG. 6C is a bar graph showing that SXR can activate through inducible, but not uninducible, CYP3 promoter elements. The ability of SXR to activate tk-CYP3-luc response elements in response to various inducers was tested. Results are shown for 50 μM compound and represent the mean of triplicate determinations.

□=refampicin; and ■=corticosterone

Figure 7A:
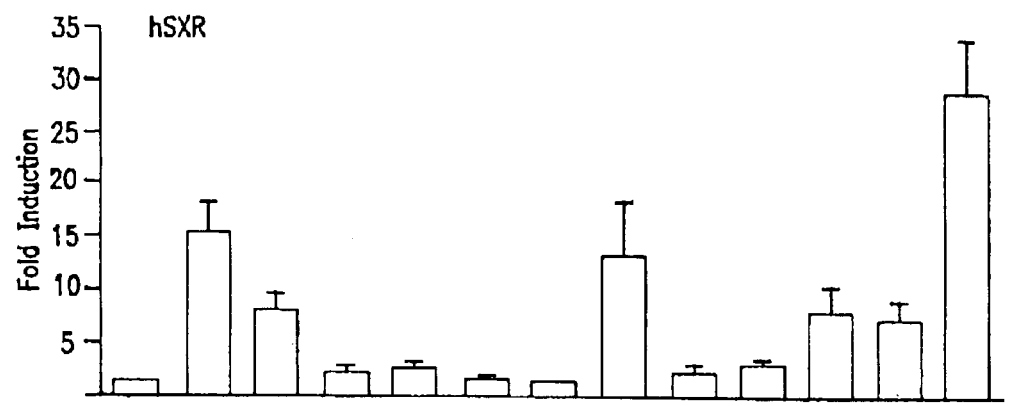
Figure 7B:
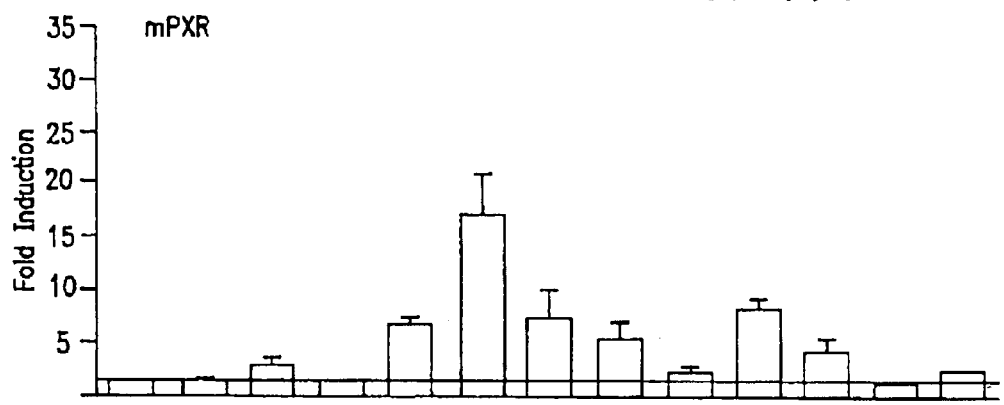
Figure 7C:
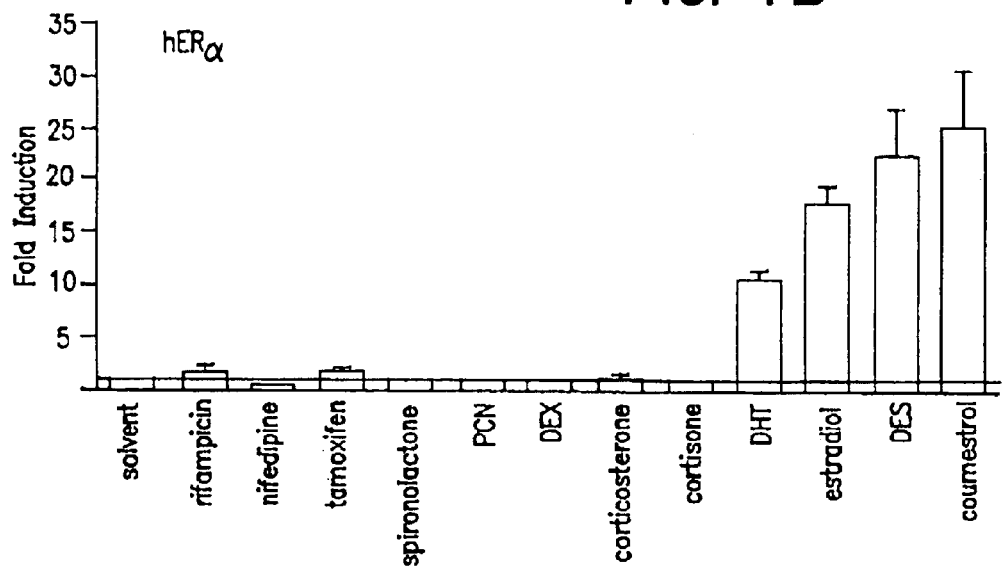

FIGS. 7A–C are bar graphs illustrating the ability of a panel of compounds to activate a representative of three members of the nuclear receptor superfamily, human SXR (FIG. 5A); mouse PXR (FIG. 5B); and human estrogen receptor alpha (hERα). Results are shown for 50 μM of compound tested, except that the concentration of tamoxifen was 5 μM; and the concentration of dexamethasone (DEX) was 50 μM in FIGS. 7A and 7B and 5 μM in FIG. 7C. Column 1=solvent; column 2=rifamipicin; column 3=nifedipine; column 4=tamoxifen; column 5=spironolactone; column 6=PCN; column 7=DEX; column 8=corticosterone; column 9=cortisone; column 10=DHT; column 11=estradiol; column 12=DES; and column 13=coumestrol.

Figure 7D:
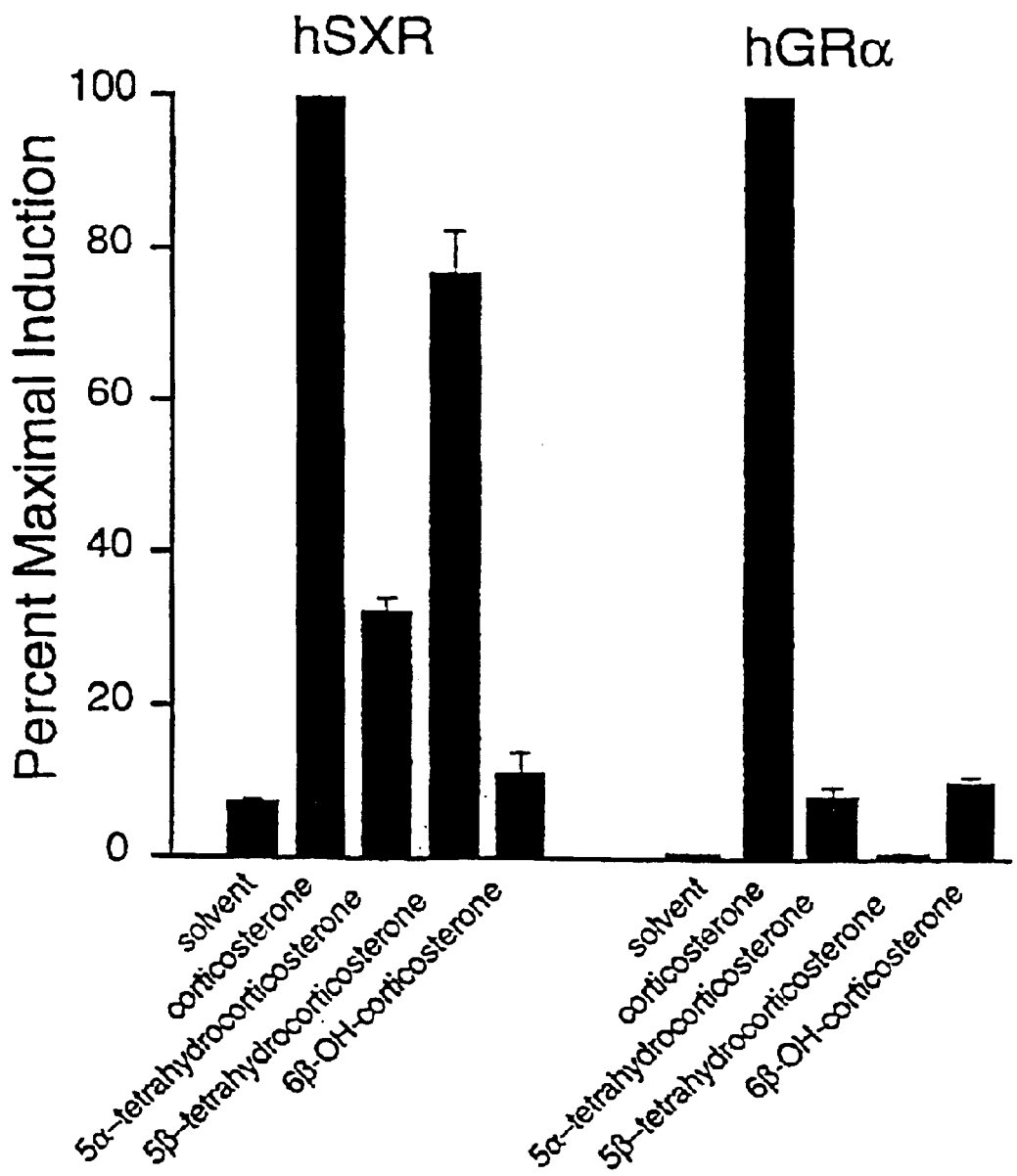

FIG. 7D is a bar graph illustrating that reduction of the 4–5 double bond in corticosterone does not inactivate the compound as an agonist of hSXR. 6β-hydroxylated, non-reduced, 5α and 5β reduced forms of corticosterone were tested for their ability to activate GAL-hSXR on tk(MH100)$_4$-luc (lefthand group of 5 columns) and hGRα on MTV-luc at 50 μM (righthand group of 5 columns).

Similar results were obtained using full-length SXR. In each group of columns: column 1=solvent; column 2=corticosterone; column 3=5α-tetrahydrocorticosterone; column 4=5β-tetrahydrocorticosterone; and column 5=6β-OH-corticosterone.

A DETAILED DESCRIPTION OF THE INVENTION

In accordance with the present invention, a new class of receptors has been identified that are part of the steroid/thyroid hormone superfamily of receptors, a representative member of which has been designated SXR (or "steroid X receptor"). Invention receptors are characterized by:

forming a heterodimer with retinoid X receptor (RXR), binding to a (direct or inverted) repeat response element motif based on the half site AGTTCA, activating transcription through response elements found in steroid inducible P450 genes in response to a wide variety of natural and synthetic steroid hormones, and being prominently expressed in the liver and the intestine.

Invention receptor(s) comprise a protein of approximately 464 amino acids (see SEQ ID NO:2), which is most closely, although distantly, related to the Xenopus benzoate X receptor (BXR), the vitamin D3 receptor (VDR) and the constitutively activated receptor (CAR). Also provided herein is a 2068 bp cDNA which encodes an example of invention receptors (see SEQ ID NO:1 and FIG. 1A).

In accordance with the present invention, there are also provided method(s) for modulating metabolism of one or more steroid and/or xenobiotic compound(s) in a subject in need thereof, comprising administering to the subject an effective amount of a modulator of a SXR polypeptide that activates transcription of an endogenous gene operatively associated with a steroid and xenobiotic receptor X (SXR) response element.

In one particular aspect of the invention, a method is provided for preventing steroid toxicity in a subject undergoing treatment of a disease state involving therapeutic administration of one or more steroid compounds. In this embodiment, the invention method comprises administering to such a patient an effective amount of one or more agonists for an invention SXR polypeptide to activate transcription of an endogenous gene operatively associated with one of the invention SXR response elements, thereby preventing increase of the overall level of steroid and xenobiotics above a physiologically acceptable level. The steroid toxicity can result from dietary build-up. (e.g., of estrogens) from drug overdose, (e.g., caused by misdiagnosis of a disease state) or from a drug interaction between therapeutically administered compounds, or between one or more endogenous steroids and one or more dietary and/or therapeutically administered compounds.

Commonly administered therapeutic drugs that tend to accumulate or cause a drug interaction in certain individuals leading to an increase in the overall level of steroid and xenobiotics above a physiologically suitable level include tamoxifen, ralozifene (e.g., in treatment of breast cancer), vitamin K (e.g., in treatment of osteoporosis), and calcium channel blockers, such as nifedipine, and the like.

In yet another aspect, the invention provides a method for slowing clearance of a therapeutic steroid or xenobiotic from a subject, such as a human or other mammal, which comprises administering to the subject an effective amount of an antagonist for a SXR polypeptide that activates transcription of an endogenous gene operatively associated with a SXR response element. This aspect of the invention method is useful for controlling too rapid clearance of one or more therapeutic steroids and/or xenobiotics caused by a drug interaction between such compounds.

For example, rifampin (i.e., rifampicin), or an active derivative or analog thereof, is commonly used to treat tuberculosis. Yet rifampin tends to cause hepatic clearance of other therapeutic drugs, such as oral contraceptives (leading to unwanted pregnancy), warfarin (leading to decreased prothrombin times), cyclosporine and prednisone (leading to organ rejection or exacerbations of any underlying inflammatory condition), and verapamil and diltiazem (necessitating increased dosage requirements). A similar situation develops in treatment of osteoporosis with the therapeutic steroid Vitamin K. To overcome these problems, in accordance with the present invention, an effective amount of a SXR polypeptide antagonist is administered to the patient to slow clearance of the therapeutic steroids from the subject.

In yet another aspect, the invention provides a screening assay for determining whether a test compound, or a combination thereof, will activate the invention SXR polypeptide. The assay comprises contacting a host cell line containing an SXR receptor polypeptide, preferably a human or rabbit cell line, with one or more test compound(s) in an appropriate culture medium, wherein the host cell line further contains a reporter vector comprising a promoter that is operable in the cell line operatively linked to an invention SXR response element for activation thereof, and DNA encoding a reporter protein operatively linked to the promoter for transcription of the DNA. The invention assay further includes determining whether the reporter protein is present (i.e., expressed by the cell line), wherein a determination that the reporter is present indicates the test compound activates the SXR polypeptide (i.e., an agonist), and a determination that the reporter is not present in the assay predicts the test compound does not activate the invention SXR polypeptide (i.e., not an agonist).

It has been discovered that compound(s) that will activate transcription of the DNA contained in the above-described reporter vector are strong agonists of the invention SXR receptor and fall into the category of "steroids and/or xenobiotics" as the term is used herein.

It has further been discovered that compounds determined by the above assay to activate transcription of the DNA contained in the above described reporter vector are likely to become involved in a drug interaction if administered to a subject at a therapeutic level. More particularly, there is a greater than 30% likelihood, for example a likelihood of about 45% to about 90%, or from about 50% to about 70%, that a therapeutic dose of such a compound will cause a drug interaction as described herein, with other steroids and/or xenobiotics, whether such compounds are endogenously produced, result from dietary sources, or are therapeutically administered to a subject in treatment of a particular disease state. Therefore, in one particular aspect, the invention assay is a method for screening compounds, particularly potential therapeutic compounds, to determine those with at least a 30% likelihood of becoming involved in an undesirable drug interaction if administered to a subject at a therapeutic level. Such a screening assay is a valuable adjunct to any drug development program because it will identify those drug candidates that must be thoroughly screened in vivo to determine their safety, thereby reducing the cost of drug development in general while preventing the possibility that a drug candidate will prove potentially dangerous due to its capacity to cause unhealthy elevation of steroid levels or too rapid clearance of another therapeutically administered compound due to a "drug interaction."

Figure 1B:
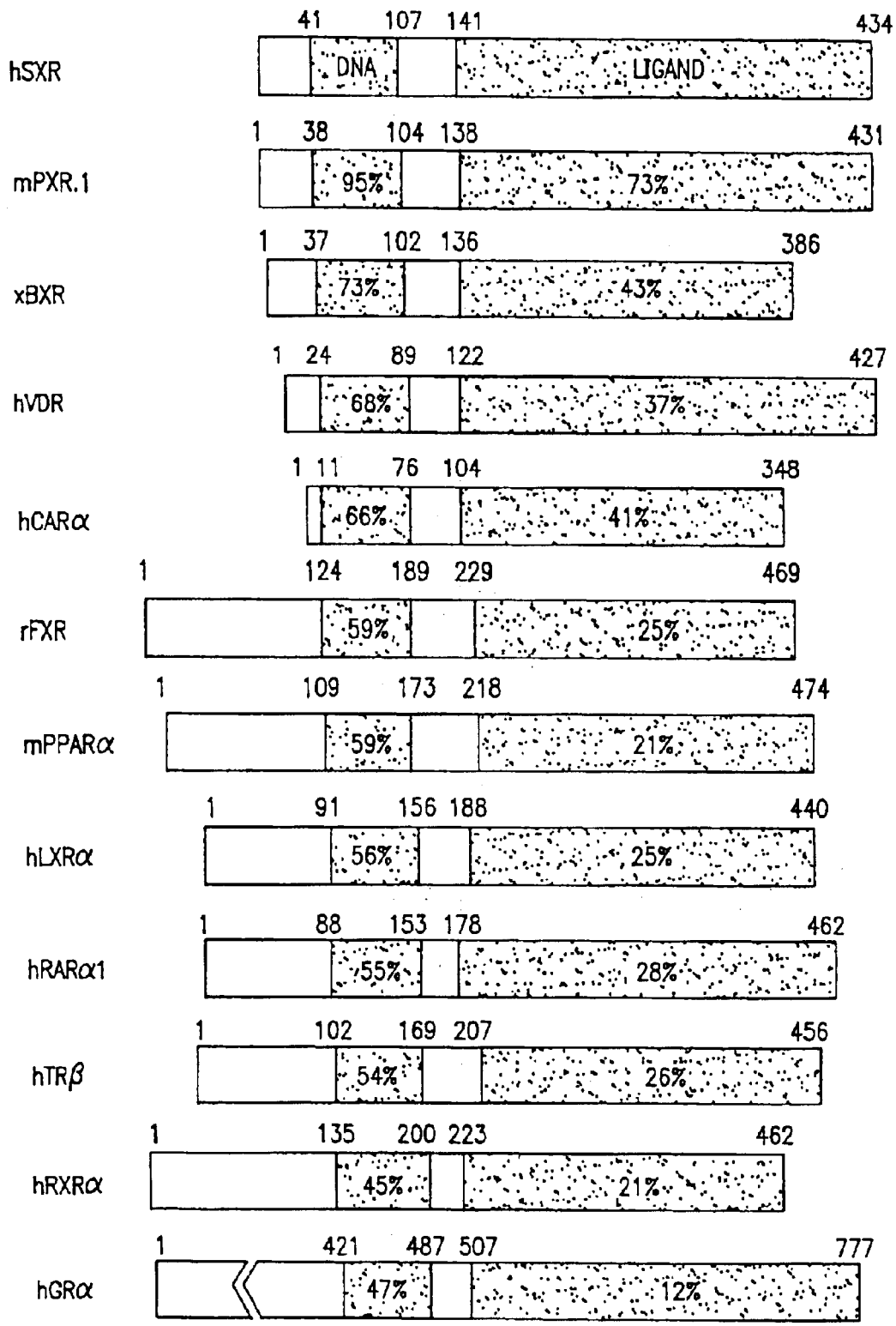
FIG. 1B presents a schematic comparison between SXR and other RXR partners (e.g., the Xenopus benzoate X receptor (xBXR), the human vitamin D3 receptor (hVDR), the human constitutively active receptor-alpha (hCARα), the rat farnesoid X receptor (rFXR), the human peroxisome proliferator activated receptor alpha (hPPARα), the human liver-derived receptor X (LXR.α), the human retinoic acid receptor alpha-1 (hRARα-1), the human thyroid hormone receptor beta (hTRβ), the human retinoid X receptor alpha (RXRα) and the human glucocorticoid receptor alpha (hGRα)). Ligand-binding domain boundaries follow those for the canonical nuclear receptor ligand-binding domain (Wurtz et al., *Nature Struct. Biol.* 3:87–94, 1996). Similarity between RXR and other receptors is expressed as percent amino acid identity (indicated in Arabic numerals above each clone). Amino acid residues in the sequences were aligned using the program GAP (Devereaux et al., *Nucl. Acids Res.* 12:387–395, 1984). DNA=DNA binding domain and LIGAND=ligand binding domain.

The invention methods are based upon the discovery of a new class of receptors identified as part of the steroid/thyroid hormone superfamily of receptors. The invention receptor, designated herein "the steroid and xenobiotic receptor" (SXR), has been identified as a potential human homolog(s) of the Xenopus benzoate 'X' receptor, BXR (Blumberg et al., *Genes Dev.* 12:1269–1277, 1998). The cDNA encoding one member of the SXR class (SEQ ID NO:1) predicts a protein of 434 amino acids (SEQ ID NO: 2) (FIG. 1A), which is 73% identical to BXR in the DNA-binding domain (DBD) and 43% identical in the ligand binding domain (LBD) (FIG. 1B). SXR is most closely related to the recently described pregnane 'X' receptor (Kliewer et al., *Cell* 92:73–82, 1998) (95% identical in the DNA binding domain (DBD), and 73% identical in the ligand binding domain (LBD). SXR is more distantly related to the vitamin D3 receptor and the orphan receptor CAR (Baes et al., *Mol. Cell. Biol.* 14:544–1551, 1994) (FIG. 1B). Other than these receptors, SXR shows no more similarity to other nuclear receptors than the different receptor subfamilies do to each other (FIG. 1B). It is known that true homologs among nuclear receptors typically share considerable similarity, especially in the DBD.

SXR can be further characterized as having a DNA binding domain of about 67 amino acids with 9 Cys residues (i.e., amino acid residues 41–107, as set forth in SEQ ID NO:2), wherein the SXR DNA binding domain has about 73% amino acid identity with the DNA binding domain of the Xenopus benzoate X receptor. Alternatively, or in addition, SXR can be further characterized as having a ligand binding domain of at least about 294 amino acids (i.e., at least amino acid residues 141–434, as set forth in SEQ ID NO:2), wherein said ligand binding domain has about 43% amino acid identity with the ligand binding domain of the Xenopus benzoate X receptor (FIG. 1B).

A presently preferred SXR polypeptide according to the invention is a polypeptide having substantially the same amino acid sequence as shown in SEQ ID NO:2. As employed herein, the phrase "substantially the same," whether used in reference to the nucleotide sequence of DNA, the ribonucleotide sequence of RNA, or the amino acid sequence of protein, refers to sequences that have slight and non-consequential sequence variations from the actual sequences disclosed herein. Species that are substantially the same are considered to be equivalent to the disclosed sequences and as such are within the scope of the appended claims. In this regard, "slight and non-consequential sequence variations" means that sequences that are substantially the same as the DNA, RNA, or proteins disclosed and/or claimed herein are functionally equivalent to the sequences disclosed and/or claimed herein. Functionally equivalent sequences will function in substantially the same manner to produce substantially the same compositions as the nucleic acid and amino acid compositions disclosed and claimed herein. In particular, functionally equivalent DNAs encode proteins that are the same as those disclosed herein or proteins that have conservative amino acid variations, such as substitution of a non-polar residue for another non-polar residue or a charged residue for a similarly charged residue. These changes include those recognized by those of skill in the art not to substantially alter the tertiary structure of the protein.

An especially preferred SXR polypeptide according to the invention method is a polypeptide having the same amino acid sequence as shown in SEQ ID NO:2.

Thus, the terms "SXR receptor" and "SXR polypeptide" are interchangeable as used herein and are intended to include functional fragments of the invention SXR polypeptide(s). Such fragments include peptides having the DNA binding and/or the ligand binding properties of SXR, e.g. the DNA binding domain thereof (e.g. amino acid residues 41–107 as shown in SEQ ID NO:2), the ligand binding domain thereof (e.g., amino acid residues 141–434 as shown in SEQ ID NO:2).

The modulator(s) useful in the practice of the invention method(s) include both agonists and antagonists of the SXR polypeptide. When the modulator is an agonist, the modulator is characterized as one which activates transcription of a gene encoding a compound active in catabolism of a therapeutic, endogenous, or dietary steroid, or of certain dietary lipids, which gene is characterized by being associated with a SXR response element such that activation of the response element results in transcription of the gene. Generally the gene encodes an enzyme effective in metabolism of one or more steroids or xenobiotic substances, such as dietary lipids and phytoestrogens, and also includes a nucleotide sequence that encodes a SXR response element, for example, one having a direct repeat of an AGGTCA half site (the DR half site) separated by a spacing of 3, 4, or 5 nucleotides, or a direct repeat of a one nucleotide variant thereof, such as a direct repeat of an AGTTCA half site (the βDR half site) separated by 3, 4, or 5 nucleotides. The response element can also comprise an inverse repeat of the half site AGGTCA separated by a 6 nucleotide spacer, or an inverse repeat of a one nucleotide variant thereof, separated by a 6 nucleotide spacer. Examples of response elements suitable for use in practice of the invention methods can be selected from the following:

DR-3,4,5=AGGTCAN$_n$AGGTCA, wherein n is 3 (SEQ ID NO: 36), 4 (SEQ ID NO: 37), or 5 (SEQ ID NO: 38);

βDR-3,4,5=AGTTCAN$_n$TGAACT, wherein n is 3 (SEQ ID NO: 22), 4 (SEQ ID NO: 39) or 5 (SEQ ID NO: 40) and IR-6=TGAACTN$_n$AGGTCA, wherein n is 6 (SEQ ID NO: 23), and the like.

Those of skill in the art will recognize that any combination of nucleotides can be used to make up the 3, 4, 5, or 6 nucleotide spacer between the repeated half sites (i.e., N$_n$ in SEQ ID NOS: 36, 37, 38, 22, 39, 40 or 23).

Such response elements are generally found in genes encoding catabolic enzymes, such as CYP2A1, CYP2A2, CYP2C1, CYP3A1, CYP3A2, an P450 oxidoreductase, uridine diphosphate glucuronosyltransferase, or a glucuronosyl transferase, transcription of which genes is activated or suppressed by practice of the invention method(s).

Representative examples of agonists capable of activating transcription of such catabolic enzymes include molecules that have high-affinity receptors, such as progesterone, testosterone, estrogen and corticosterone, as well as their reduced catabolites that are, for the most part, inactive on the high-affinity receptors. In addition to the natural steroids, SXR is activated by synthetic steroids, including PCN and dexamethasone, as well as by xenobiotic drugs, phytosteroids, and the like. The presently preferred agonists include corticosterone, rifampicin, nifedipine, corticosterone, DES, estradiol, dihydrotestosterone, pregnenolone, progesterone, and PCN, with corticosterone being the strongest known activator.

When the modulator is an antagonist of SXR, the modulator functions in one or more of the following ways: (1) to block binding of the polypeptide to the SXR response element, (2) to inhibit formation of a heterodimer of the polypeptide and a retinoid X receptor, or (3) to inhibit binding of a ligand to the ligand binding domain of SXR or an invention SXR polypeptide. For example, the antagonist can inhibit formation of a heterodimer between a retinoid X receptor and the SXR or an invention SXR polypeptide by blocking the docking site between the molecules. Alternatively, an antagonist can inhibits binding of a ligand to the ligand binding domain of the SXR or invention SXR polypeptide by binding to the active site of the ligand (i.e., the portion of the ligand that binds to the ligand binding domain). Any of a variety of compounds that will accomplish one or more of these goals can be used as an antagonist in the invention methods. For example, an antibody that binds to SXR or to a RXR so as to prevent formation of the a SXR:RXR heterodimer can be used as an antagonist in the practice of the present invention. Similarly, an antibody that blocks the ligand binding domain of the SXR receptor without activating transcription of the target gene so as to prevent binding of the ligand to the ligand binding domain will function as an antagonist in the invention method(s).

One of skill in the art will be aware of, or can readily devise, additional polypeptides or nucleotides that will act as antagonists of gene transcription in the invention method(s).

In accordance with another embodiment of the present invention, there are provided heterodimer complexes which consist of the above-described receptor polypeptide and RXR or other silent partner therefor.

In accordance with yet another embodiment of the present invention, there are provided isolated nucleic acids which encode the above-described receptor polypeptides. As used herein, the phrase "isolated nucleic acid" means a nucleic acid that is in a form that does not occur in nature. One means of isolating a nucleic acid encoding a polypeptide is to probe a mammalian genomic library with a natural or artificially designed DNA probe using methods well known in the art. DNA probes derived from the SXR gene are particularly useful for this purpose. DNA and cDNA molecules that encode SXR polypeptides can be used to obtain complementary genomic DNA, cDNA or RNA from human, mammalian (e.g., mouse, rat, rabbit, pig, and the like), or other animal sources, or to isolate related cDNA or genomic clones by the screening of cDNA or genomic libraries, by methods described in more detail below. Examples of nucleic acids are RNA, cDNA, or isolated genomic DNA encoding SXR.

Exemplary DNAs include those which encode substantially the same amino acid sequence as shown in SEQ ID NO:2 (e.g., a contiguous nucleotide sequence which is substantially the same as nucleotides 583–1884 shown in SEQ ID NO:1). Presently preferred DNAs include those which encode the same amino acid sequence as shown in SEQ ID NO:2 (e.g., a contiguous nucleotide sequence which is the same as nucleotides 583–1884 shown in SEQ ID NO:1).

As used herein, nucleotide sequences which are substantially the same share at least about 90% identity, and amino acid sequences which are substantially the same typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention. As readily recognized by those of skill in the art, various ways have been devised to align sequences for comparison, e.g., the Blosum 62 scoring matrix, as described by Henikoff and Henikoff in *Proc. Natl. Acad. Sci. USA* 89:10915 (1992). Algorithms conveniently employed for this purpose are widely available (see, for example, Needleman and Wunsch in *J. Mol. Biol.* 48:443 (1970).

In accordance with still another embodiment of the present invention, there are provided nucleic acid constructs comprising the above-described nucleic acid, operatively linked to regulatory element(s) operative for transcription of the nucleic acid and expression of the polypeptide in an animal cell in culture. There are also provided cells containing such a construct, optionally containing a reporter vector comprising:

(a) a promoter that is operable in said cell,
(b) a SXR response element, and
(c) DNA encoding a reporter protein,
   wherein the reporter protein-encoding DNA is operatively linked to the promoter for transcription of the DNA, and
   wherein the promoter is operatively linked to the SXR response element for activation thereof.

In accordance with a further embodiment of the present invention, there are provided methods of making invention receptor polypeptide(s), said methods comprising culturing cells containing an expression vector operable in said cells to express a DNA sequence encoding said polypeptide.

In accordance with a still further embodiment of the present invention, there are provided probes comprising labeled single-stranded nucleic acid, comprising at least 20 contiguous bases in length having substantially the same sequence as any 20 or more contiguous bases selected from bases 1–2068, inclusive, of the DNA illustrated in SEQ ID NO:1, or the complement thereof. An especially preferred probe of the invention comprises at least 20 contiguous bases in length having substantially the same sequence as any 20 or more contiguous bases selected from bases 583–1884, inclusive, of the DNA illustrated in SEQ ID NO:1, or the complement thereof.

Those of skill in the art recognize that probes as described herein can be labeled with a variety of labels, such as for example, radioactive labels, enzymatically active labels, fluorescent labels, and the like. A presently preferred means to label such probes is with $^{32}$P. Such probes are useful, for example, for the identification of receptor polypeptide(s) characterized by being responsive to the presence of one or more steroid and/or xenobiotic to regulate the transcription of associated gene(s), said method comprising hybridizing test DNA with a probe as described herein under high stringency conditions (e.g., contacting probe and test DNA at 65° C. in 0.5 M $NaPO_4$, pH 7.3, 7% sodium dodecyl sulfate (SDS) and 5% dextran sulfate for 12–24 hours; washing is then carried out at 60° C. in 0.1× SSC, 0.1% SDS for three thirty minute periods, utilizing fresh buffer at the beginning of each wash), and thereafter selecting those sequences which hybridize to said probe.

In another aspect of the invention, the above-described probes can be used to identify invention receptor polypeptide(s), or functional fragments thereof, said methods comprising hybridizing test DNA with a probe as described herein under high stringency conditions, and selecting those sequences which hybridize to said probe.

In yet another aspect of the invention, the above-described probes can be used to assess the tissue sensitivity of an individual to exposure to steroid and steroid-like compounds by determining SXR mRNA levels in a given tissue sample. It is expected that an individual having a high level of SXR mRNA (or protein) will be sensitive to the presence of significant levels of steroid and xenobiotic compounds, such as are encountered in many foods, or as a result of overproduction and/or reduced ability to degrade steroids, as seen in such diseases as Cushing's syndrome, virilism and hirsutism in females, polycystic ovarian syndrome, and the like.

In accordance with yet another embodiment of the present invention, there are provided antibodies which specifically bind the above-described receptor polypeptides. Preferably, such antibodies will be monoclonal antibodies. Those of skill in the art can readily prepare such antibodies having access to the sequence information provided herein regarding invention receptors.

Thus, the above-described antibodies can be prepared employing standard techniques, as are well known to those of skill in the art, using the invention receptor proteins or portions thereof as antigens for antibody production. Both anti-peptide and anti-fusion protein antibodies can be used (see, for example, Bahouth et al. *Trends Pharmacol Sci.* 12:338–343 (1991); *Current Protocols in Molecular Biology* (Ausubel et al., eds.) John Wiley and Sons, New York (1989)). Factors to consider in selecting portions of the invention receptors for use as immunogen (as either a synthetic peptide or a recombinantly produced bacterial fusion protein) include antigenicity, uniqueness to the particular subtype, and the like.

The availability of such antibodies makes possible the application of the technique of immunohistochemistry to monitor the distribution and expression density of invention receptors. Such antibodies could also be employed for diagnostic and therapeutic applications.

In accordance with a further embodiment of the present invention, binding assays employing SXRs are provided, useful for rapidly screening a large number of compounds to determine which compounds (e.g., agonists and antagonists) are capable of binding to the receptors of the invention. Subsequently, more detailed assays can be carried out with initially identified compounds, to further determine whether such compounds act as agonists or antagonists of invention receptors.

The invention binding assays may also be employed to identify new SXR-like ligands. Test samples (e.g., biological fluids) may also be subjected to invention binding assays to detect the presence or absence of SXR or SXR ligands.

Another application of the binding assay of the invention is the assay of test samples (e.g., biological fluids) for the presence or absence of SXR. Thus, for example, tissue homogenates from a patient displaying symptoms thought to be related to over- or under-production of steroids can be assayed to determine if the observed symptoms are related to the presence of SXR.

The binding assays contemplated by the present invention can be carried out in a variety of ways, as can readily be identified by one of skill in the art. For example, competitive binding assays can be employed, as well as radioimmunoassays, ELISA, ERMA, and the like.

In accordance with yet another embodiment of the present invention, there is provided a method of testing a compound for its ability to regulate transcription-activating effects of invention receptor polypeptide(s), said method comprising assaying for the presence or absence of reporter protein upon contacting of cells containing said receptor polypeptide and reporter vector with said compound;
  wherein said reporter vector comprises:
    (a) a promoter that is operable in said cell,
    (b) a hormone response element, and
    (c) DNA encoding a reporter protein,
      wherein said reporter protein-encoding DNA is operatively linked to said promoter for transcription of said DNA, and
      wherein said promoter is operatively linked to said hormone response element for activation thereof.

Hormone response elements suitable for use in the above-described assay method comprise direct or inverted repeats of at least two half sites (each having the sequence RGBNNM, as defined herein). In each half site, RGBNNM:
  R is selected from A or G;
  B is selected from G, C, or T;
  each N is independently selected from A, T, C, or G; and
  M is selected from A or C;
    with the proviso that at least 4 nucleotides of said—RGBNNM—sequence are identical with the nucleotides at corresponding positions of the sequence AGTTCA.

Those of skill in the art recognize that the spacing between half sites can vary over a considerable range, typically falling in the range of about 0 up to 15 nucleotides. When the half sites are oriented as direct repeats, it is presently preferred that the half sites be separated by a spacer of 3, 4 or 5 nucleotides. Those of skill in the art recognize that any combination of 3, 4 or 5 nucleotides can be used as the spacer. Direct repeat response elements having a spacer of 4 nucleotides (e.g., SEQ ID NOS:6, 7 or 16) are presently preferred. When the half sites are oriented as inverted repeats, it is presently preferred that the half sites be separated by a spacer of 4, 5 or 6 nucleotides. Those of skill in the art recognize that any combination of 4, 5 or 6 nucleotides can be used as the spacer.

Optionally, the above-described method of testing can be carried out in the further presence of ligand for invention receptors, thereby allowing the identification of antagonists of invention receptors. Those of skill in the art can readily carry out antagonist screens using methods well known in the art. Typically, antagonist screens are carried out using a constant amount of agonist, and increasing amounts of a putative antagonist (i.e., a competitive assay). Alternatively, antagonists can be identified by rendering the receptor constitutively active (e.g., by adding a strong, constitutively-active activator to the receptor) and screening for compounds which shut down the resulting constitutively-active receptor.

In accordance with another aspect of the present invention, there are provided methods to identify compounds which are agonists of steroid X receptor (SXR), but which neither agonize nor antagonize other steroid receptors, said method comprising:
  detecting in a first assay system the presence or absence of reporter protein upon contacting of cells containing SXR and reporter vector with said compound;
  wherein said reporter vector comprises:
    (a) a promoter that is operable in said cell,
    (b) an SXR response element, and
    (c) DNA encoding a reporter protein,
      wherein said reporter protein-encoding DNA is operatively linked to said promoter for transcription of said DNA, and
      wherein said promoter is operatively linked to said SXR response element for activation thereof;
  detecting in a second assay system the presence or absence of reporter protein upon contacting of cells containing a steroid hormone receptor other than SXR and reporter vector with said compound;
  wherein said reporter vector comprises:
    (a) a promoter that is operable in said cell,
    (b) a response element for said receptor other than SXR, and
    (c) DNA encoding a reporter protein,
      wherein said reporter protein-encoding DNA is operatively linked to said promoter for transcription of said DNA, and wherein said promoter is operatively linked to said response element for said receptor other than SXR for activation thereof; and identifying those compounds which induce production of reporter in said first assay, but not in said second assay, as compounds which are agonists of steroid X receptor (SXR), but neither agonists nor antagonists of other steroid receptors.

Thus, it can readily be seen that invention methods can be used to identify a variety of therapeutically useful compounds. The compounds identified as described herein can be used for the treatment of a wide variety of indications, such as, for example:

a) Cushing's syndrome (hypercortisolism), which manifests as increased cortisol levels, leading to numerous problems including obesity, fatigue, hypertension, edema and osteoporosis;

b) virilism and hirsutism in females due to overproduction of testosterone;

c) androgen excess due to polycystic ovarian syndrome, which manifests as greatly increased circulating levels of dehydroepiandrosterone;

d) enzymatic defects which lead to accumulation of specific steroids, such as:
   1) 21-hydroxylase deficiency leading to increased synthesis of 17-hydroxy-progesterone and androgens;
   2) 11β-hydroxylase deficiency leading to deoxycortisol and deoxycorticosterone accumulation and attendant hypertension;
   3) 3β-hydroxysteroid dehydrogenase deficiency resulting in accumulation of pregnenolone and dehydroepi-androsterone, leading to sexual ambiguity in both sexes;
   4) 17-hydroxylase deficiency, which prevents cortisol synthesis but leads to accumulation of corticosterone and deoxycorticosterone, resulting in hypertension and aberrant development of secondary sexual characteristics in both sexes;

f) ameliorate the effect of substances in the diet and/or environment which act as endocrine disruptors, e.g., estrogens which may be involved in breast, colorectal and prostate cancers (Adlercreutz and Mazur in *Ann. Med.* 29:95–120 (1997); and the like.

Compounds which are specific agonists for SXR without acting as either agonists or antagonists for other steroid receptors will find particular utility where other steroid compounds have been used for their catatoxic properties, while tolerating the negative effects of such therapeutic use (presumably caused by the undesirable activation of previously described steroid receptors, e.g., glucocorticoid receptor). Compounds which are specific agonists for SXR without acting as either agonists or antagonists for other steroid receptors will find particular utility where other steroid compounds have been used for their catatoxic properties, while tolerating the negative effects of such therapeutic use (presumably caused by the undesirable activation of previously described steroid receptors, e.g., glucocorticoid receptor).

In accordance with a still further embodiment of the present invention, there are provided methods for modulating process(es) mediated by invention receptor polypeptides, said methods comprising conducting said process(es) in the presence of at least one agonist, antagonist or antibody raised against invention receptor.

In accordance with yet another embodiment of the present invention, there are provided methods for inducing the expression of steroid degradative enzymes, said method comprising activating SXR. Exemplary steroid degradative enzymes contemplated for expression herein include steroid hydroxylases, and the like.

In accordance with the present invention, it has further been discovered that induction of some xenobiotic-metabolizing enzymes by pharmacological levels of steroids is regulated by SXR, a class of broad-specificity, low-affinity, nuclear hormone receptors. One benefit of such a receptor-based system is that it induces the expression of xenobiotic metabolizing enzymes only at activator levels sufficiently high to interfere with normal endocrine function. It also makes biological sense that the expression of enzymes with broad substrate specificity, such as cytochrome P450s, can be induced by a receptor responsive to a diverse group of activators, some of which can be substrates for the induced enzymes.

To determine whether the activity of SXR was ligand-dependent, mixtures of natural and synthetic compounds were tested for their ability to activate SXR in transfection-based assays (see Example 3). A mixture containing dehydroepiandrosterone (DHEA) and pregnenolone was observed to be active, suggesting that SXR might be a new steroid receptor. To characterize its response properties, a large variety of steroids, including intermediate and major products of known steroid biosynthetic pathways were tested. Surprisingly, most of these compounds were active, although there were clear differences in potency (see FIG. 2). Indeed, most of the more than 70 steroids tested showed some activity at high doses. Activation was dependent on the ligand binding domain of SXR since both full-length receptors and GAL4-receptor ligand binding domain chimeras showed similar activity, whereas there was no activation of reporter gene expression in experiments with reporter alone or reporter plus GAL4 DNA-binding domain.

The most potent and efficacious activator of the numerous steroids tested is corticosterone. Estradiol and dihydrotestosterone are also remarkably effective activators while aldosterone and 1,25 dihydroxy vitamin D3 are inactive, even at 50 mM. Although ligands for the classical steroid receptors do show some overlap in receptor specificity, there is no example of a nuclear receptor that can be activated by so many different types of steroids. This broad ligand specificity of SXR parallels that of PPARα, which can be activated by an extremely diverse group of dietary fatty acids at micromolar levels (see, for example, Forman et al., in *Proc. Natl. Acad. Sci. USA* 94:4312 (1997) and Gottlicher et al., in *Proc. Natl. Acad. Sci. USA* 89:4653 (1992)).

The diversity of steroids showing activity on SXR suggests that this novel class of receptors might be able to sense cumulative, as well as individual steroid levels, predicting that combinations of activators might be more active than the individual components. As shown in FIG. 3, a cocktail containing 10 steroids, each at 10 mM concentration (i.e., an overall steroid concentration of 100 mM), was considerably more active than its individual components at 10 mM, a concentration at which most were inactive. These results confirm that SXR is a broad-specificity, low-affinity, steroid-activated receptor.

An important requirement for physiologic homeostasis is the removal and detoxification of various endogenous hormones and xenobiotic compounds with biological activity. Much of the detoxification is performed by cytochrome P450 enzymes, many of which have broad substrate specificity and are inducible by a bewildering array of compounds, including steroids. The ingestion of dietary steroids and lipids induces the same enzymes and thus, must be integrated into a coordinated metabolic pathway. Instead of possessing hundreds of receptors, one for each inducing compound, the class of receptors described herein indicates the existence of a class of broad-specificity, low-affinity nuclear receptors that monitor total steroid levels and induce the expression of genes encoding xenobiotic metabolizing enzymes. These results indicate the existence of a steroid sensor mechanism for removal of elevated levels of steroids (or steroid-like compounds) from circulation via broad-specificity, low-affinity receptors which represent a novel branch of the nuclear receptor superfamily.

Indeed, a search of the GENBANK database for genes containing putative SXR response elements identified a number of steroid hydroxylases, e.g., CYP2A1, CYP2A2, CYP2C1, CYP2C6, CYP3A1, CYP3A2, P450 oxidoreductase and UDP-glucuronosyltransferase, as candidate target genes. The relevant portions of these sequences are as follows:

DR-3

```
                                        (SEQ ID NO:3)
rCYP3A1   tagac AGTTCA tga AGTTCA tctac
                                        (SEQ ID NO:4)
rCYP3A2   taagc AGTTCA taa AGTTCA tetac
                                        (SEQ ID NO:5)
rUGT1A6   actgt AGTTCA taa AGTTCA catgg
```

DR-4

```
                                        (SEQ ID NO:6)
rbCYP2C1  caatc AGTTCA acag GGTTCA ccaat
                                        (SEQ ID NO:7)
rP450R    cac AGGTGA gctg AGGCCA gcagc AGGTCG aaa
```

DR-5

```
                                        (SEQ ID NO:8)
rCYP2A1   gtgca GGTTCA actgg AGGTCA acatg
                                        (SEQ ID NO:9)
rCYP2A2   gtgct GGTTCA actgg AGGTCA gtatg
                                        (SEQ ID NO:10)
rCYP2C6   agtct AGTTCA gtggg GGTTCA gtctt
                                        (SEQ ID NO:11)
hCYP2E1   gagat GGTTCA aggaa GGGTCA ttaac
```

Figure 4:
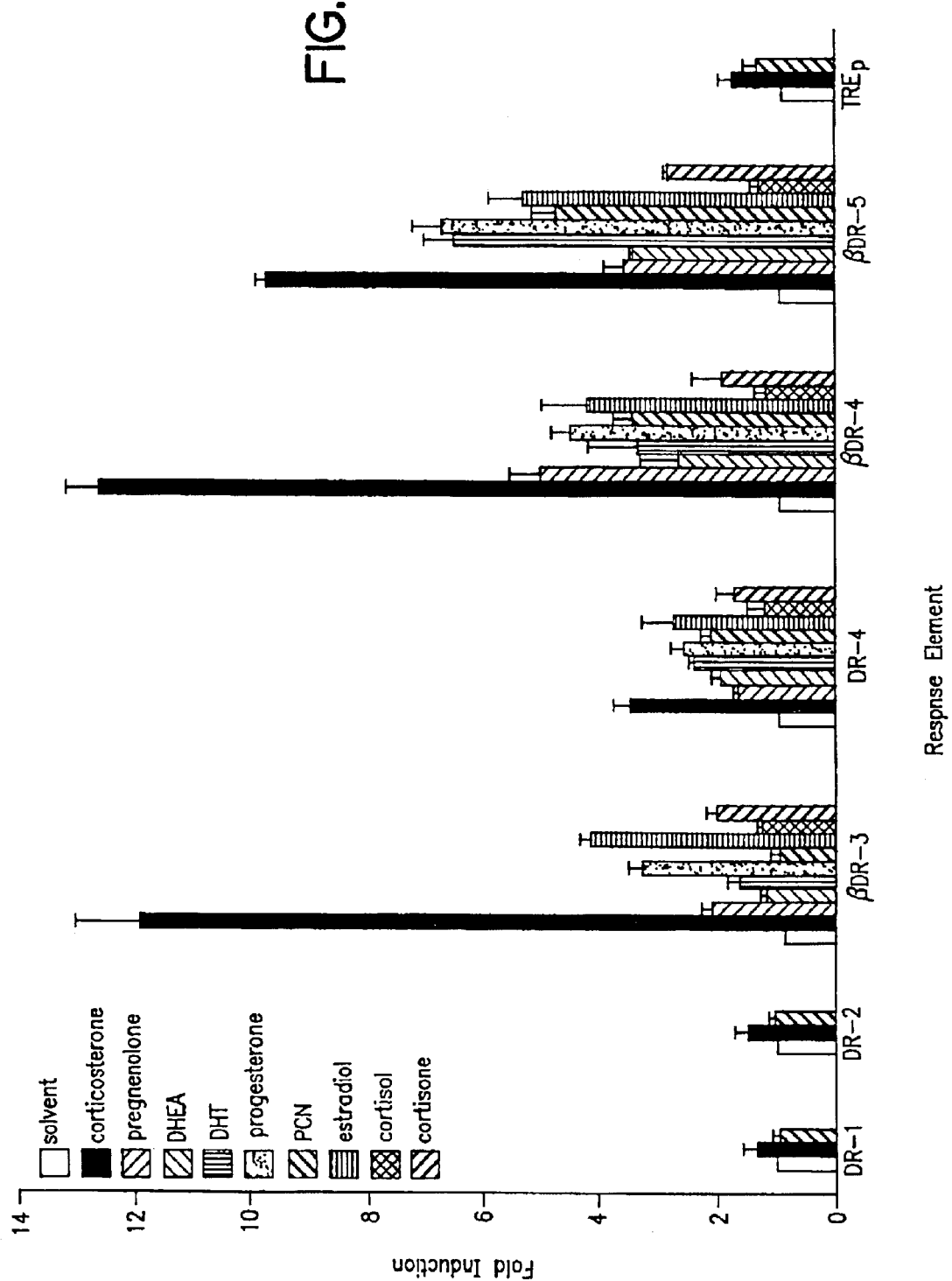
FIG. 4 illustrates the broad activator and response element specificity of SXR. Full-length SXR was tested in cotransfection experiments for its ability to activate elements similar to those in FIG. 3 in response to a panel of steroids at 50 mM. DR-1,2 and TREp were only very slightly activated, hence results are shown only for corticosterone and PCN. The data shown are expressed as mean fold induction over solvent control +/−standard error from triplicate assays.

The data shown in FIG. 4 verify that SXR can activate DR-3, DR-4 and DR-5 elements that are present in these genes. In the series of transfections described in Example 3, corticosterone along with pregnenolone, progesterone, DHT, estradiol and PCN are consistently among the best activators. Dexamethasone, cortisone and DHEA are in the intermediate group with little response from either aldosterone or cortisol (see FIG. 4). Consistent with the DNA-binding data, maximal activities are achieved on βDR-3, βDR-4 and βDR-5 elements.

Thus, SXR response elements are found in genes encoding steroid hydroxylases, P450 oxidoreductase, and glucuronosyl transferase. These enzymes can metabolize endogenous as well as xenobiotic compounds and are legitimate targets for a receptor that is activated by pharmacological levels of steroids. SXR is highly expressed in liver, the major expression site of xenobiotic metabolizing enzymes, suggesting that the steroid sensor mechanism is active in the appropriate tissue. In addition, prominent expression is also found in the intestine. Although less is known about the role of this tissue in steroid or xenobiotic metabolism, it is certainly possible that the intestine plays a role in regulating the metabolism of dietary, and perhaps endogenous, steroids. Taken together, these data strongly support the existence of a class of low-affinity, broad-specificity nuclear hormone receptor(s), such as SXR, which function as intracellular "steroid sensor(s)".

Figure 5:
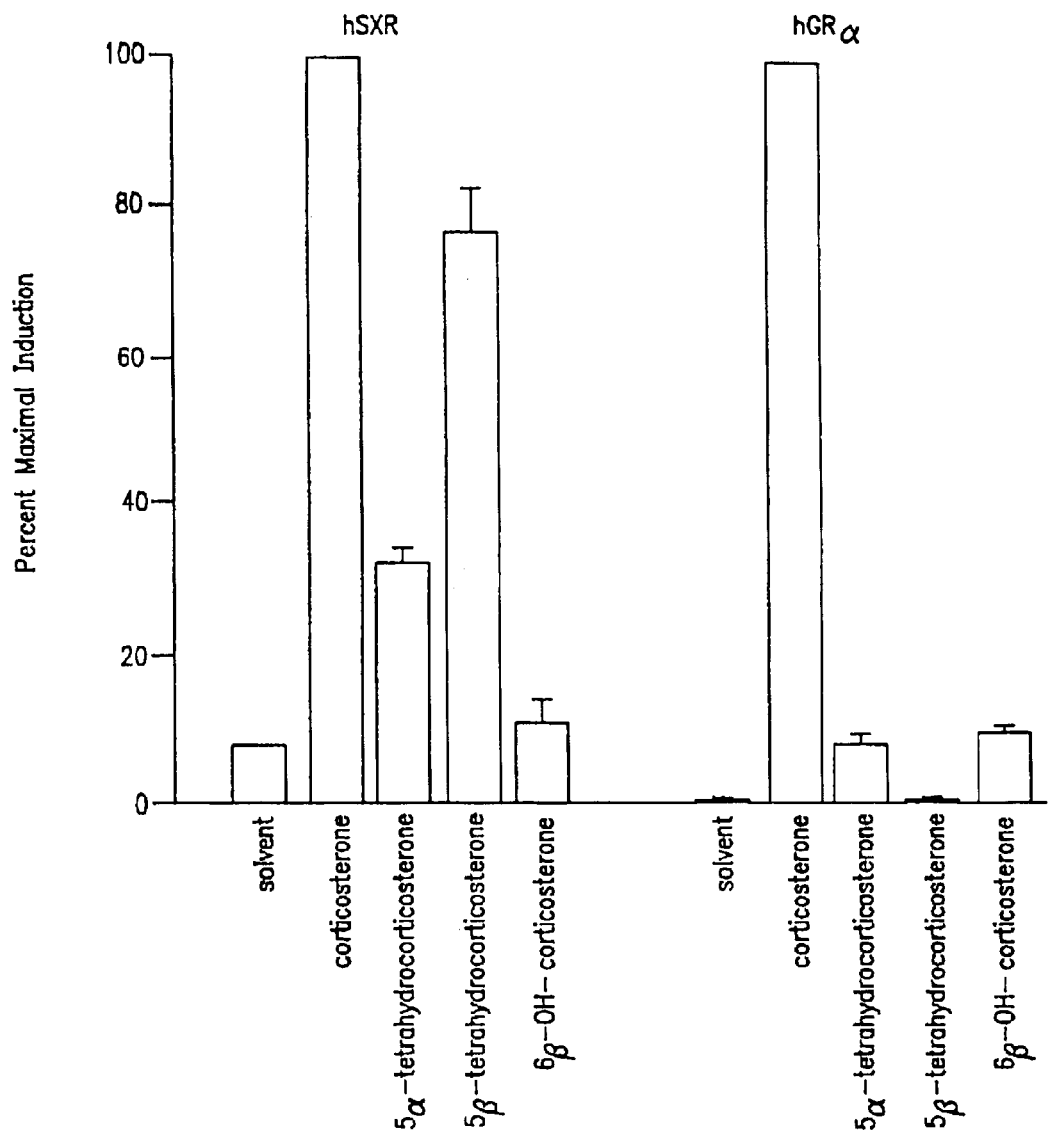
FIG. 5 further illustrates the broad ligand specificity of SXR. Thus, it is seen that reduction of the 4–5 double bond does not inactivate corticosterone. 6β-hydroxylated, non-reduced, 5α and 5β reduced forms of corticosterone were tested for their ability to activate GAL-SXR on tk(MH100)$_4$-luc and hGRα on MTV-luc at 50 mM. Similar results were obtained using full-length SXR.

The localization of apparent SXR-responsive elements in genes encoding steroid hydroxylases raises the question of whether products of steroid catabolism, such as reduced or hydroxylated corticosterone derivatives, could also activate SXR. FIG. 5 shows that both 5α and 5β reduced forms of corticosterone are effective SXR activators whereas 5α is slightly active and 5β is completely inactive on GR. While a few 5α-reduced steroids remain active (e.g., dihydrotestosterone), virtually all 5β-reduced steroids are unable to activate classical steroid receptors (see Russell and Wilson in *Ann. Rev. Biochem.* 63:25 (1994)). Accordingly, the activation of SXR by 5β-reduced steroids reveals a previously unidentified role for these compounds in gene regulation.

6β-hydroxy corticosterone is virtually inactive on SXR and slightly active on GR (see FIG. 5). CYP3A genes, which contain SXR-activatable response elements, catalyze the hydroxylation of many steroids at the 6 position. Therefore, the inability of 6β-hydroxy-corticosterone to activate SXR suggests that 6-hydroxylation is a potential regulatory step in the SXR signaling pathway.

Thus, in support of the role for members of the SXR class of nuclear receptors proposed herein, it has been demonstrated herein that SXR is activated by an extremely diverse group of steroids and their metabolites, including molecules that have high-affinity receptors such as progesterone, testosterone, estrogen and corticosterone as well as their reduced catabolites that are, for the most part, inactive on the high-affinity receptors. In addition to the natural steroids, SXR is activated by synthetic steroids including PCN and dexamethasone. These data provide a molecular explanation for the paradoxical induction of the CYP3A genes (a.k.a. $P450_{PCN}$) by both glucocorticoid receptor agonists and antagonists since the cyp3A genes harbor a SXR-activatable response element in the promoter region that has been shown to be responsible for PCN and glucocorticoid induction (see Burger et al. supra and Gonzalez et al. supra). Whereas such a result is unexplainable by regulation of traditional, high-affinity steroid receptors, such behavior is consistent with the observed properties of the newly characterized steroid X receptor.

Further tests were conducted to discover whether P450s known to be inducible by PCN and other steroids could be SXR targets. The primary human steroid-inducible P450 is the CYP3A4 gene (Molowa et al., *Proc. Natl. Acad. Sci.* (USA) 83:5311–5315, 1986, Beaune et al., *Proc. Natl. Acad. Sci.* (USA) 83:8064–8068, 1986). Unlike the rat and mouse CYP3A genes, all of which contain a DR-3 response element that SXR can activate (FIG. 4), the human and rabbit promoters do not contain such an element. Inducibility of CYP3A4 by steroids and xenobiotics has been localized to an 19 base pair element that is functional in transient transfection assays (Barwick et al., *Mol. Pharmacol.* 50:10–16, 1996). This element contains the IR-6 motif (TGAACTcaaaggAGGTCA) (SEQ ID NO:24). Similar elements have been identified in human CYP3A5, and CYP3A7 and in rabbit CYP3A6 genes (FIG. 6B) (Barwick, supra, 1996). Tests conducted to determine the ability of SXR to bind a series of inverted repeat elements with spacings from zero to six nucleotides determined that only an IR-6 response element, showed significant binding. As with the direct repeats, these results indicate the binding was dependent on formation of a RXR:SXR heterodimer. In addition, competition binding experiments demonstrated little difference in the apparent affinity of SXR:RXR heterodimers for the βDR-4 and CYP3A4 IR-6 response elements. In accord with the known inducibility of the parent promoters, SXR was shown to activate reporter constructs containing the CYP3A4, but not the CYP3A5 or CYP3A7 motifs.

Compounds known to induce CYP3A4 were also shown to activate the invention SXR. The compounds tested included drugs, such as rifampicin and nifedipine; steroid antagonists, such as tamoxifen, spironolactone and PCN; natural and synthetic steroids, such as dexamethasone, diethylstilbestrol, estradiol, dihydrotestosterone, corticosterone and cortisone; and phytoestrogens, such as coumestrol, equol and genistein. Of these compounds, rifampicin, nifedipine, corticosterone, estradiol, DES, and coumestrol were the most potent activators (FIG. 7A. The mouse receptor PXR responded poorly to these inducers, but was preferentially activated by PCN, a weak activator of SXR (FIG. 7B). PXR is reported to be preferentially activated by pregnanes (21-carbon steroids such as dexamethasone (DEX) and pregnenolone) (Kliewer, supra, 1998); however, our tests showed that PXR is similarly activated by 19-carbon androstanes, like testosterone, and 18-carbon estranes, like estradiol (FIG. 7B). Similar results were obtained with other natural steroids, including progesterone, pregnenolone and dihydroethanoic acid (DHEA).

To demonstrate that the activation of SXR and PXR by high steroid concentrations is not a general property of all steroid receptors, parallel tests were conducted to determine the activation of the human estrogen receptor (ER) by the same panel of compounds. The only endogenous steroids tested that activated the ER were DHT and estradiol. The synthetic ER agonist, DES, and the phytoestrogens, including coumestrol (FIG. 7C), also activated the human estrogen receptor.

Because the invention SXR-responsive elements are localized in genes encoding steroid hydroxylases, products of steroid catabolism, such as reduced or hydroxylated corticosterone derivatives, were tested for activation of SXR. The results of these tests shown in FIG. 7D illustrate that both 5α and 5β reduced forms of corticosterone are effective SXR activators; however, 5α is slightly active, and 5β is completely inactive on GR. While a few 5α-reduced steroids remain active (e.g., dihydrotestosterone), 5β-reduced steroids fail to activate classical steroid receptors (Russell and Wilson, Ann. Rev. Biochem. 63:25–61. 1994). Therefore, the activation of SXR by 5β-reduced steroids may reflect a previously undetected regulatory pathway for these compounds. In addition, the virtual inactivity of, 6β-hydroxy corticosterone on SXR (FIG. 6D), suggests that CYP3A4 catalyzed hydroxylation is a potential definitive regulatory step in steroid metabolism.

These results indicate that the induction of some xenobiotic-metabolizing enzymes by pharmacological levels of steroids, drugs, and xenobiotic compounds is regulated by a broad-specificity sensor, rather than numerous specific receptors. SXR is a novel member of the nuclear receptor superfamily that is activated by a diverse group of steroids and their metabolites. Direct regulation by a broad-specificity sensor, such as the invention SXR, is biologically economical since much of the detoxification and catabolism of such compounds is mediated by cytochrome P450 enzymes, particularly members of the CYP3A family, which both metabolize, and are induced by, a wide spectrum of diverse compounds, including steroids.

Based on the above-described studies, a number of relationships have been discovered among target genes, the SXR, and its activators that support the role of the SXR as a broad sensitivity sensor responsible for regulating cumulative levels of steroids and xenobiotics. First, SXR is expressed in tissues which catabolize steroids and xenobiotics, particularly in liver, the major expression site of steroid and xenobiotic metabolizing enzymes, and in the intestine. Although less is known about the role of gut tissue in steroid metabolism, the gut is known to play an important role in first pass metabolism of dietary, and orally-administered compounds (Holtbecker et al., Drug Metab. Dispos. 24:1121–1123, 1996; and Kolars et al., Lancet 338:1488–1490, 1991). For example, CYP3A4 is highly expressed in enterocytes (Kolars et al., J. Clin. Invest. 90:1871–1878, 1992). Thus, SXR is expressed at high levels in two key tissues for steroid and xenobiotic catabolism. Second, catabolic enzymes expressed in tissues that express SXR are induced by the invention SXR. SXR response elements have been discovered in the well-characterized CYP3A4 promoter as well as those of P450 oxidoreductase, CYP2A, CYP2C, CYP2E and glucuronosyl transferase, which are all known to be involved in steroid and xenobiotic catabolism (F. J. Gonzalez, Trends Pharmacol. Sci. 13:346–352, 1992). Third, compounds known to induce catabolic enzymes activate the invention SXR, including drugs (such as rifampicin and nifedipine), steroid receptor agonists and antagonists (such as estrogen and tamoxifen); bioactive dietary compounds (such as phytoestrogens), and the like. In particular, CYP3A4 is known to be inducible (Rendic and Di Carlo, 1997) by virtually all the compounds applicants have identified as SXR activators. Lastly, products of early catabolic steps, such as reduced steroids, activate SXR, ensuring their complete inactivation and elimination. Taken together, these relationships support the role of the SXR as a broad-specificity sensor operative to regulate homeostasis of steroids and xenobiotics.

Figure 6C:
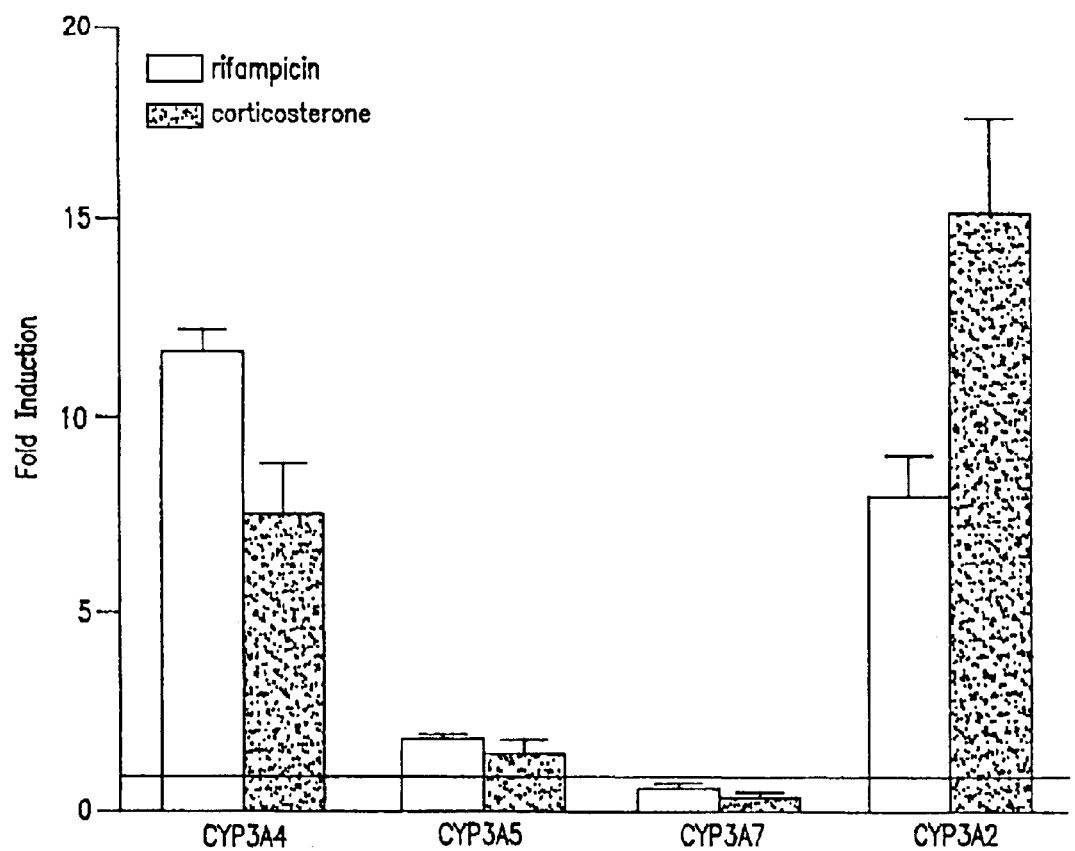

Activation of SXR also provides a molecular explanation for the paradoxical induction of the CYP3A genes (a.k.a. $P450_{PCN}$) by both glucocorticoid receptor agonists and antagonists and for the differential response of orthologous enzymes in different species. The inducible CYP3A genes harbor response element in their promoters that has been shown to be responsible for PCN and glucocorticoid induction (Barwick, supra, 1996; Burger, supra, 1992; Gonzalez, supra, 1986; Schuetz and Guzelian, supra, 1984; and Kliewer, supra, 1998). Applicants have discovered that these response elements can be activated by the invention SXR (FIGS. 6A and 6C). Despite their common role in steroid and xenobiotic catabolism, CYP3A genes from different species, and particularly the glucocorticoid-responsive promoter elements, show considerable differences in the pharmacology of their inducers (Barwick, supra, 1996). For example, PCN is a strong inducer of rat CYP3A2 and CYP3A3, but a weak inducer of human CYP3A4 and rabbit CYP3A6. On the other hand, rifampicin is a strong inducer of the human and rabbit genes encoding such enzymes but not the rat genes (Barwick, supra, 1996).

However, when the response elements from such genes are tested by transient transfection into primary hepatocytes from rats or rabbits, the responsiveness changes to that of the host cell type. For example, glucocorticoid-responsive elements from the rat CYP3A2 and CYP3A3 promoters were induced by DEX in both rat and rabbit hepatocytes, by PCN only in rat hepatocytes, and by rifampicin only in rabbit hepatocytes (Barwick, supra, 1996). Similarly, the glucocorticoid-responsive element from the human CYP3A4 promoter was inducible by DEX in both rat and rabbit hepatocytes, by PCN only in rat hepatocytes, and by rifampicin only in rabbit hepatocytes (Barwick, supra, 1996). The activation profiles in rat cells correspond to the responsiveness of PXR to the inducers (FIG. 6C); whereas the responsiveness in rabbit cells corresponds to that of SXR. Since the rabbit 3A6 promoter lacks the rodent DR-3 element, but has the human IR-6 element (Barwick, supra, 1996), it can be inferred that rabbit liver will likely have a receptor more closely related to SXR than to PXR. Thus, the pharmacology of SXR and PXR activation explains the different inducibility of the rat, rabbit, and human members of the cytochrome P4503A family. This discovery suggests that rabbit hepatocytes behave more like their human counterparts than do rodent hepatocytes, and that rabbits are perhaps better suited to testing for human-like drug interaction than rodents.

One additional member of the new branch of the nuclear receptor superfamily called the steroid and xenobiotic receptor has been discovered in mouse tissue. Screening of a mouse liver cDNA library at reduced stringency resulted in the identification of 39 cDNAs, all of which encoded PXR. 1. Orthologous nuclear receptors typically share greater than 90% amino acid identity in the ligand binding domain when comparing rodent and human receptors (e.g., RARα-98% human/mouse (h/m), PPARγ-98% h/m, GR-95% h/m, TRβ-98% h/rat, ERα-89% h/m). Therefore, PXR and SXR may represent α and β subtypes of the steroid and xenobiotic nuclear receptor family. This conclusion is supported by the distinct pharmacological properties of the receptors, as illustrated in the Examples herein. Further screening of mouse and human liver cDNA libraries has failed to identify other family members. It is also possible that PXR and SXR represent unusually divergent orthologous genes. If this were correct, the divergence might reflect adaptation of the receptor to the difference between the diets of rodents and primates and the requirement for the receptor to respond to appropriate food-borne compounds.

To obtain the invention receptor, commercially obtained Northern blots of multiple human tissues were probed by full-length SXR cDNA (SEQ ID NO: 1), as described in Example 1 herein. The results showed that SXR mRNA is expressed at high levels in human liver and at more moderate levels in human intestine. Exposures of the Northern blots for longer than 24 hours did not reveal expression in any other tissues. Multiple mRNAs were detected, ranging from 3500 nt to larger than 9000 nt. Comparison of the sequences of the four cDNAs obtained reveals shared protein coding and 5' untranslated sequences, but a different 3' end for each of the four. These sequence differences may be due to alternative polyadenylation.

Electrophoretic mobility shift assays were employed to determine the ability of SXR to heterodimerize with RXR and to analyze the selectivity and specificity of SXR DNA binding as described in Example 4 herein. Receptors that heterodimerize with RXR typically bind to direct repeats of AGGTCA or closely related sequences (Mangelsdorf and Evans, supra, 1995). SXR alone and in combination with RXR was tested against a series of response elements differing in the spacing between half sites from 0 to 15 nucleotides. No binding was seen on classic steroid response elements. In contrast, strong binding was selective to a DR-4 motif with minimal binding to DR-3 and DR-5, and no binding to other spacings. When the variant AGTTCA (βDR) half site was used, strong binding was seen on βDR-4 and βDR-5, and significant, but reduced, binding to βDR-3. These results demonstrate that SXR binds DNA as a heterodimer with RXR rather than as a homodimer like the classical steroid receptors (Beato, supra, 1995).

To determine whether the activity of SXR was ligand-dependent, mixtures of natural and synthetic compounds were tested for their ability to activate SXR in transfection-based assays. A mixture containing DHEA and pregnenolone was active, suggesting that SXR might be a new steroid receptor. To characterize more fully the response properties of the receptors, a large variety of steroids, including intermediate metabolites and major products of known steroid biosynthetic pathways were tested for ability to activate the invention SXR. As illustrated by the results shown in FIG. 2, most of these compounds were active, although there were clear differences in potency. Of the more than 70 steroids tested, most showed some activity at high doses. It was also discovered that both full-length receptors and GAL4-receptor ligand binding domain chimeras showed similar activity; but no activation of reporter gene expression was detected in experiments with reporter alone or reporter plus GAL4 DNA-binding domain (FIG. 2). These results indicate that activation is dependent on the ligand-binding domain of SXR.

The most potent and efficacious activator of the numerous steroids tested was corticosterone (FIG. 2). Estradiol and dihydrotestosterone were also remarkably effective activators, while aldosterone and 1,25 dihydroxy vitamin D3 were inactive, even at a concentration of 50 μM (FIG. 2). Although ligands for the classical steroid receptors do show some overlap in receptor specificity, there is no known example of a nuclear receptor that can be activated by so many different types of steroids. This broad ligand specificity of the invention SXR parallels that of PPARα, which is activated by a very diverse group of dietary fatty acids at micromolar levels (Forman et al., *Proc. Natl. Acad. Sci. USA* 94:4312–4317, 1997; Gottlicher et al., *Proc. Natl. Acad. Sci. USA* 89:4653–4657, 1992; Kliewer et al., *Proc. Natl. Acad. Sci.* (*USA*) 94:4318–4323, 1997).

A search of the GENBANK database for genes containing potential SXR response elements identified the steroid hydroxylases CYP2A1, CYP2A2, CYP2C1, CYP2C6, CYP3A1, CYP3A2, P450 oxidoreductase, and UDP-glucuronosyl-transferase as candidate target genes (FIG. 6A). The search identified DR-3, DR-4 and DR-5 elements present in these genes, which indicates that such compounds activate the invention SXR. Similarly, the transfection-based assays described in Example 4, which were conducted to test the ability of steroids and xenobiotics to activate SXR response elements showed that corticosterone along with pregnenolone, progesterone, dihydrotestosterone (DHT), estradiol, and PCN are consistently among the best activators. Dexamethasone, cortisone, and DHEA are in the group of intermediate activators, and there is little response from either aldosterone or cortisol (FIG. 4). Consistent with the DNA-binding data, maximal activities induced by these activators was achieved in steroid inducible P450 genes containing βDR-3, βDR-4, and βDR-5 response elements (FIG. 4).

The term "effective amount" as applied to a SXR polypeptide agonist or antagonist according to the invention means the quantity necessary to modulate metabolism of one or more steroid and/or xenobiotic compounds to a desired level, for example, a level effective to treat, cure, or alleviate the symptoms of a disease state for which the therapeutic compound is being administered, or to establish homeostasis. Alternatively, when an agonist according to the invention is employed to prevent steroid toxicity in a subject therapeutically administered one or more therapeutic steroid and/or xenobiotic compounds in treatment of a disease state, the term "effective amount" is an amount necessary to bring the overall level of steroids and xenobiotic compounds to a safe level, for example as determined by blood tests of the individual being treated for the effects of steroid toxicity, or to alleviate the symptoms of steroid toxicity as determined by the physician. Similarly, the amount of a SXR polypeptide antagonist according to the invention used to slow clearance of a therapeutic steroid or xenobiotic compound is an amount necessary to raise the blood level of the particular therapeutic compound to a therapeutic level and hence treat or alleviate the symptoms of the disease state for which the therapeutic steroid or xenobiotic compound is being administered. Since individual subjects may present a wide variation in severity of symptoms and each drug or active agent has its unique therapeutic characteristics, the precise mode of administration, dosage employed and treatment protocol for each subject is left to the discretion of the practitioner.

Amounts effective for the particular therapeutic goal sought will, of course, depend on the severity of the condition being treated, and the weight and general state of the subject. Various general considerations taken into account in determining the "effective amount" are known to those of skill in the art and are described, e.g., in Gilman et al., eds., *Goodman And Gilman's: The Pharmacological Bases of Therapeutics*, 8th ed., Pergamon Press, 1990; and *Remington's Pharmaceutical Sciences*, 17th ed., Mack Publishing Co., Easton, Pa., 1990, each of which is herein incorporated by reference.

Pharmaceutical formulations of the SXR polypeptide agonists or antagonists of the present invention can be used in the form of a solid, a solution, an emulsion, a dispersion, a micelle, a liposome, and the like, wherein the resulting formulation contains one or more of the agonists or antagonists contemplated for use in the practice of the present invention, as active ingredients, in admixture with an organic or inorganic carrier or excipient suitable for enteral or parenteral applications. The active ingredients may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compounds (i.e., one or more SXR polypeptide agonist or antagonist) are included in the pharmaceutical formulation in an amount sufficient to produce the desired effect upon the target process, condition or disease.

Pharmaceutical formulations containing the active ingredients contemplated herein may be in a form suitable for oral use, for example, as tablets, troches, lozenges, aqueous or oily suspensions, dispersible powders or granules, emulsions, hard or soft capsules, or syrups or elixirs. Formulations intended for oral use may be prepared according to any method known in the art for the manufacture of pharmaceutical formulations. In addition, such formulations may contain one or more agents selected from a sweetening agent (such as sucrose, lactose, or saccharin), flavoring agents (such as peppermint, oil of wintergreen or cherry), coloring agents and preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents such as calcium carbonate, lactose, calcium phosphate, sodium phosphate, and the like; (2) granulating and disintegrating agents such as corn starch, potato starch, alginic acid, and the like; (3) binding agents such as gum tragacanth, corn starch, gelatin, acacia, and the like; and (4) lubricating agents such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredients are mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, or olive oil.

The pharmaceutical formulations may also be in the form of a sterile injectable solution or suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,4-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, or synthetic fatty vehicles, like ethyl oleate, or the like. Buffers, preservatives, antioxidants, and the like, can be incorporated as required.

Formulations contemplated for use in the practice of the present invention may also be administered in the form of suppositories for rectal administration of the active ingredients. These formulations may be prepared by mixing the active ingredients with a suitable non-irritating excipient, such as cocoa butter, synthetic glyceride esters of polyethylene glycols (which are solid at ordinary temperatures, but liquify and/or dissolve in the rectal cavity to release the active ingredients), and the like.

The invention will now be described in greater detail by reference to the following non-limiting examples.

EXAMPLE 1 cDNA Identification

SXR was identified from a human genomic library (Clontech) hybridized with a full-length cDNA encoding Xenopus BXR (Blumberg et al., 1998a) under reduced stringency conditions (hybridization in 0.5 M $NaPO_4$ pH 7.0, 7% sodium dodecyl sulfate (SDS), 5% dextran sulfate at 65° C. overnight, washing three times twenty minutes in 2× standard saline citrate solution (0.15M saline containing 0.015M sodium citrate, pH 7) (SSC), 0.1% SDS at 37° C.). Restriction mapping and Southern blot analysis showed that three exons were contained within the 9 kb EcoRI hybridizing fragment. This fragment was used to probe a Northern blot of multiple types of human tissue (Clontech) at high stringency (hybridization as above, washing twice for 20 minutes in 0.1× SSC, 0.1% SDS at 50° C.) and hybridization was detected in liver. A human liver cDNA library (Stratagene, La Jolla, Calif.) was subsequently screened using the same conditions, and four independent clones were identified. Each of these clones was sequenced on both strands within the protein coding region. DNA sequences were compiled and aligned using the programs of Staden (R. Staden, *Nucl. Acids Res.* 14:217–231, 1986), University of Wisconsin Genetics Computer Group (Devereaux et al., *Nucl. Acids Res.* 12:387–395, 1984). Database searching was performed using the BLAST network server at the National Center for Biotechnology Information (Altschul et al., *J. Mol. Biol.* 215:403–410, 1990). PXR was isolated from a mouse liver cDNA library (Stratagene) by screening with the SXR protein coding region at reduced stringency (5× SSC, 43% formamide, 5× Denhardts, 0.1% SDS, 0.1 mg/ml denatured, sonicated salmon sperm DNA at 37° C.). Three, twenty minute washes were performed in 0.5× SSC, 0.1% SDS at 50° C.

EXAMPLE 2

Ability of SXR to Heterodimerize With RXR

The protein coding region of SXR was PCR amplified and subcloned into NcoI and BamHI sites of the vector pCDG1 (Blumberg, supra, 1998a) using ExoIII-mediated ligation independent cloning (Li and Evans, *Nucl. Acids Res.* 25, 4165–4166, 1997). During this process the putative initiator Leu was converted to Met with a Kozak consensus sequence CC<u>ATG</u>G. The actual response elements and the number of copies are as follows: the base vector is tk-luc in all cases (Hollenberg et al., *Nature* 318:635–641, 1985):

DR-1, tk(ApoAI)$_4$ (Ladias and Karathanasis, *Science* 251:561–565, 1991);

DR-2, tk(Hox-B1-RARE)$_2$ (Ogura and Evans,*Proc. Natl. Acad. Sci.* (USA) 92:387–391, 1995);

βDR-3, tk(CYP3A2)$_3$ (Kliewer et al., *Cell* 92:73–82, 1998),

DR-4, tk(MLV-TRE)$_2$ (Umesono et al., *Cell* 65:1255–1266, 1991);

βDR-4, tk(LXRE)$_3$ (Willy et al., *Genes Dev.* 9:1033–1045, 1995);

βDR-5, tk(βRARE)$_3$ (Sucov et al., *Proc. Natl. Acad. Sci.* (U.S.A.) 87:5392–5396, 1990);

TRE$_p$, tk(TRE$_p$)$_2$ (Umesono et al., supra, 1991).

Direct repeat 0–15 (DR-0 up to DR-15) oligonucleotides employed herein had the following sequences:

Similarly, the PXR.1 protein coding region was PCR amplified and subcloned into a NcoI-BamHI cut in pCDG1, while amino acids 104 to 431 were subcloned into CMX-GAL4. Reporter plasmids were constructed by synthesizing three-copy response elements and subcloning into a HindIII-BamHI cut in pTk-luc (Hollenberg et al., *Cell* 49:39–46, 1987).

CV-1 cells were maintained in Dulbecco's Modified Eagle's Medicine (DMEM) containing 10% resin-charcoal stripped calf bovine serum (CBS). Liposome-mediated transient transfections were performed using 1,2-bis (oleoyloxy)-3-(trimethylammonio) propane (DOTAP) reagent (Boehringer Manheim) at a concentration of 5 μg/ml in DMEM containing 10% resin charcoal stripped fetal bovine serum in 96-well format using a Beckman Biomek 1000 laboratory workstation as described in (Blumberg et al., *Proc. Natl. Acad. Sci.* (USA) 93:4873–4878, 1996). Test ligands were added the next day in DMEM containing 10% delipidated fetal bovine serum (FBS). After 18–24 hours incubation, the cells were lysed and luciferase reporter gene assays and β-galactosidase transfection control assays were performed as described in (Blumberg, supra, 1996). Reporter gene expression was normalized to the β-galactosidase transfection control and expressed as relative light units per optical density unit per minute of β-galactosidase activity, or fold induction over solvent control. Each data point represents the average of triplicate experiments +/−standard error and was replicated in independent experiments.

EXAMPLE 3

Cell Culture and Transfection Studies

To determine whether the activity of SXR was ligand-dependent, mixtures of natural and synthetic compounds were tested for their ability to activate SXR in transfection-based assays. Thus, the protein coding region of SXR was PCR amplified and subcloned into NcoI and BamHI sites of the vector pCDG1 (see Blumberg et al., supra). During this process the putative initiator Leu was converted to Met with a Kozak consensus sequence CC<u>ATG</u>G.

GAL4-SXR was constructed by cloning amino acid residues 134–446 of SXR into pCMX-GAL4 (see Perlman et al. supra). CV-1 cells were maintained in DMEM containing 10% resin-charcoal stripped calf bovine serum. Liposome-

| | | |
|---|---|---|
| DR-0: | catagtc AGGTCA AGGTCA gatcaac; | (SEQ ID NO:12) |
| DR-1: | catagtc AGGTCA t AGGTCA gatcaac; | (SEQ ID NO:13) |
| DR-2: | catagtc AGGTCA at AGGTCA gatcaac; | (SEQ ID NO:14) |
| DR-3: | catagtc AGGTCA tat AGGTCA gatcaac; | (SEQ ID NO:15) |
| DR-4: | catagtc AGGTCA tata AGGTCA gatcaac; | (SEQ ID NO:16) |
| DR-5: | catagtc AGGTCA tatat AGGTCA gatcaac; | (SEQ ID NO:17) |
| DR-6: | catagtc AGGTCA tatata AGGTCA agatcaac; | (SEQ ID NO:18) |
| DR-7: | catagtc AGGTCA tatatat AGGTCA gatcaac; | (SEQ ID NO:19) |
| DR-10: | catagtc AGGTCA tatatatata AGGTCA gatcaac; | (SEQ ID NO:20) |
| DR-15: | catagtc AGGTCA tagtagtagtagtag AGGTCA gatcaac. | (SEQ ID NO:21) |

GAL4-SXR was constructed by subcloning aa 107–434 of SEQ ID NO:2 into pCMX-GAL4 (Perlmann, supra, 1993).

mediated transient transfections were performed using DOTAP reagent (Boehringer Manheim) at a concentration of 5 mg/ml in DMEM containing 10% resin charcoal stripped fetal bovine serum in 96-well format using a Beckman Biomek 1000 laboratory workstation as previously described by Blumberg et al., in *Proc. Natl. Acad. Sci. (USA)* 93:4873 (1996)).

Ligands were added the next day in DMEM containing 10% delipidated FBS. After 18–24 hours incubation, the cells were lysed and luciferase reporter gene assays and b-galactosidase transfection control assays performed as previously described by Blumberg et al. (1996), supra. Reporter gene expression was normalized to the b-galactosidase transfection control and expressed as relative light units per O.D. per minute of b-galactosidase activity or fold induction over solvent control. Each data point (see FIG. 2) represents the average of triplicate experiments +/−standard error and was replicated in independent experiments.

EXAMPLE 4

DNA-Binding Analysis

Electrophoretic mobility shift assays were performed using in vitro transcribed, translated proteins (TNT, Promega). Proteins (1 µl each) were incubated for 20 minutes at room temperature with 100,000 cpm of Klenow-labeled probes in 10 mM Tris pH 8, 100 mM KCl, 6% glycerol, 0.05% NP-40, 1 mM dithiothreitol (DTT), 100 ng/µl poly dI:dC (Pharmacia, Piscataway, N.J.) and then electrophoresed through a 5% polyacrylamide gel in 0.5× TBE (45 mM Tris-base, 45 mM boric acid, 1 mM ethylenediaminetetraacetic acid (EDTA) at room temperature. For competition binding, protein plus unlabeled oligonucleotides at five or fifty fold molar excess were preincubated for ten minutes on ice, then labeled probes were added and incubated for 20 minutes at room temperature. Electrophoresis was as above. The IR series oligonucleotides tested had the following sequences:

| | | |
|---|---|---|
| IR-0, | agcttAGGTCATGACCTa; | (SEQ ID NO:25) |
| IR-1, | agcttAGGTCAgTGACCTa; | (SEQ ID NO:26) |
| IR-2, | agcttAGGTCAcgTGACCTa; | (SEQ ID NO:27) |
| IR-3, | agcttAGGTCAcagTGACCTa, | (SEQ ID NO:28) |
| IR-4, | agcttAGGTCAcatgTGACCTa; | (SEQ ID NO:29) |
| IR-5, | agcttAGGTCAcactgTGACCTa; | (SEQ ID NO:30) |
| IR-6, | agctttTGAACTcaaaggAGGTCA; and | (SEQ ID NO:31) |
| IR-M, | agcttACGTCATGACGTa. | (SEQ ID NO:32) |

Mutations in the IR-M nucleotide sequence prevented binding of the heterodimer to the response element.

CYP3A oligonucleotides tested had the following sequences:

```
                                              (SEQ ID NO:33)
CYP3A4, tagaataTGAACTcaaaggAGGTCAgtgagtgg;
                                              (SEQ ID NO:34)
CYP3A5, tagaataTGAACTcaaaggAGGTAAgcaaaggg;
                                              (SEQ ID NO:35)
CYP3A7, tagaataTTAACTcaatggAGGCAgtgagtgg
```

It will be apparent to those skilled in the art that various changes may be made in the invention without departing from the spirit and scope thereof, and therefore, the invention encompasses embodiments in addition to those specifically disclosed in the specification, but only as indicated in the appended claims.

---

We claim:

1. A receptor polypeptide, wherein said polypeptide is a member of the steroid/thyroid hormone superfamily and is further characterized by:
   forming a heterodimer with retinoid X receptor (RXR), wherein said heterodimer binds to a direct or inverted repeat response element comprising at least two half sites RGBNNM separated by a spacer of 0 up to 15 nucleotides,
   wherein:
      R is selected from A or G;
      B is selected from G, C or T;
      each N is independently selected from A, T, C or G; and
      M is selected from A or C;
   with the proviso that at least 4 nucleotides of said—RGBNNM—sequence are identical with the nucleotides at corresponding positions of the sequence AGTTCA,
   activating transcription of a gene under the control of a cytochrome P450 response element in response to a wide variety of natural and synthetic steroid hormones, at least including compounds that induce catabolic enzymes, steroid receptor agonists and antagonists, and bioactive dietary compounds, and
   being detectably expressed in the liver and the intestine.

2. The receptor polypeptide according to claim 1, wherein said polypeptide is further characterized by having a DNA binding domain of about 67 amino acids with 9 Cys residues, wherein said DNA binding domain has about 73% amino acid identity with the DNA binding domain of the Zenopus benzoate X receptor.

3. The receptor polypeptide according to claim 1, wherein said polypeptide is farther characterized by having a ligand binding domain of about 294 amino acids, wherein said ligand binding domain has about 43% amino acid identity with the ligand binding domain of the Xenopus benzoate X receptor.

4. The receptor polypeptide according to claim 2, wherein said polypeptide comprises a DNA binding domain having substantially the same amino acid sequence as residues 41–107 of SEQ ID NO:2, or conservative variations thereof.

5. The receptor polypeptide according to claim 3, wherein said polypeptide comprises a ligand binding domain having substantially the same amino acid sequence as residues 141–434 of SEQ ID NO:2 or conservative variations thereof.

6. The receptor polypeptide according to claim 1, wherein said polypeptide comprises substantially the same amino acid sequence as SEQ ID NO:2, or conservative variations thereof.

7. The receptor polypeptide according to claim 1, wherein said polypeptide comprises the amino acid sequence shown in SEQ ID NO:2.

8. A heterodimer complex consisting of a retinoid X receptor and a receptor polypeptide according to claim 1.

9. The receptor polypeptide according to claim 1, wherein said polypeptide is produced by culturing cells containing an expression vector operable in said cells to express a DNA sequence encoding said polypeptide.

10. A receptor polypeptide, wherein said polypeptide is encoded by a polynucleotide selected from the group consisting of
(a) polynucleotides having substantially the same sequence as SEQ ID NO:1 or SEQ ID NO:1 wherein T can also be U; and
(b) polynucleotides having at least 20 contiguous bases that hybridize under stringent conditions to the complement of SEQ ID NO:1;
wherein said polypeptide is a member of the steroid/thyroid hormone superfamily and is further characterized by:
forming a heterodimer with retinoid X receptor (RXR), wherein said heterodimer binds to a direct or inverted repeat response element comprising at least two half sites RGBNNM separated by a spacer of 0 up to 15 nucleotides,
wherein:
R is selected from A or G;
B is selected from G, C or T;
each N is independently selected from A, T, C or G; and
M is selected from A or C;
with the proviso that at least 4 nucleotides of said—RGBNNM—sequence are identical with the nucleotides at corresponding positions of the sequence AGTTCA,
activating transcription of a gene under the control of cytochrome P450 response element in response to a wide variety of natural and synthetic steroid hormones, at least including compounds that induce catabolic enzymes, steroid receptor agonists and antagonists, and bioactive dietary compounds, and
being detectably expressed in the liver and the intestine.

11. A receptor polypeptide having substantially the same amino acid sequence as set forth in SEQ ID NO:2, or conservative variations thereon wherein said polypeptide is a member of to steroid/thyroid hormone superfamily and is further characterized by:
forming a heterodimer with retinoid X receptor (RXR), wherein said heterodimer binds to a direct or inverted repeat response element comprising at least two half sites RGBNNM separated by a spacer of 0 up to 15 nucleotides,
wherein:
R is selected from A or G;
B is selected from G, C or T;
each N is independently selected from A, T, C or G; and
M is selected from A or C;
with the proviso that at least 4 nucleotides of said—RGBNNM—sequence are identical with the nucleotides at corresponding positions of the sequence AGTTCA,
activating transcription of a gene under the control of cytochrome P450 response element in response to a wide variety of natural and synthetic steroid hormones, at least including compounds that induce catabolic enzymes, steroid receptor agonists and antagonists, and bioactive dietary compounds, and
being detectably expressed in the liver and the intestine.

12. An isolated steroid X receptor (SXR) polypeptide,
wherein said receptor polypeptide comprises a ligand binding domain and a DNA binding domain;
wherein said ligand binding domain is encoded by a first polynucleotide sequence which hybridizes under stringent conditions to the complement of nucleotides 1003–1884 of SEQ ID NO:1;
wherein said ligand binding domain binds to a wide variety of natural and synthetic steroid hormones, at least including compounds that induce catabolic enzymes, steroid receptor agonists and antagonists, and bioactive dietary compounds; and
wherein said DNA binding domain is encoded by a second polynucleotide sequence which hybridizes under stringent conditions to the complement of nucleotides 703–903 of SEQ ID NO:1.

13. The receptor polypeptide according to claim 12 wherein said polypeptide is encoded by a polynucleotide having at least 90% nucleotide identity with respect to SEQ ID NO:1.

14. The receptor polypeptide according to claim 12 wherein said polypeptide has at least 95% amino acid identity with respect to SEQ ID NO:2.

15. A recombinant receptor polypeptide comprising a fusion protein, wherein said fusion protein comprises:
a DNA binding domain; and
a ligand binding domain, wherein said ligand binding domain is encoded by a polynucleotide sequence which hybridizes under stringent conditions to the complement of nucleotides 1003–1884 of SEQ ID NO:1;
wherein said fusion protein activates transcription of a gene under the control of a response element which recognizes said DNA binding domain in response to a wide variety of natural and synthetic steroid hormones, at least including compounds that induce catabolic enzymes, steroid receptor agonists and antagonists, and bioactive dietary compounds.

16. A ligand binding domain of a steroid X receptor (SXR) polypeptide,
wherein said ligand binding domain binds to a wide variety of natural and synthetic steroid hormones, at least including compounds that induce catabolic enzymes, steroid receptor agonists and antagonists, and bioactive dietary compounds, and
wherein sequence encoding said ligand binding domain hybridizes under stringent conditions to the complement of nucleotides 1003–1884 of SEQ ID NO:1.

17. The ligand binding domain according to claim 16 comprising amino acid residues 141–434 of SEQ ID NO:2, or conservative variations thereof.

* * * * *